(12) United States Patent
Saito et al.

(10) Patent No.: US 10,756,269 B2
(45) Date of Patent: Aug. 25, 2020

(54) COMPOSITION AND LIGHT EMITTING DEVICE USING THE SAME

(71) Applicant: SUMITOMO CHEMICAL COMPANY, LIMITED, Tokyo (JP)

(72) Inventors: Hiroyuki Saito, Osaka (JP); Takahiro Ueoka, Osaka (JP); Hidenobu Kakimoto, Osaka (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 161 days.

(21) Appl. No.: 15/550,936

(22) PCT Filed: Mar. 1, 2016

(86) PCT No.: PCT/JP2016/056167
§ 371 (c)(1),
(2) Date: Aug. 14, 2017

(87) PCT Pub. No.: WO2016/140205
PCT Pub. Date: Sep. 9, 2016

(65) Prior Publication Data
US 2018/0047903 A1    Feb. 15, 2018

(30) Foreign Application Priority Data
Mar. 5, 2015    (JP) ................. 2015-043254

(51) Int. Cl.
| | | |
|---|---|---|
| *H01L 51/00* | (2006.01) | |
| *C09K 11/06* | (2006.01) | |
| *C08K 5/06* | (2006.01) | |
| *C08K 5/01* | (2006.01) | |
| *C08L 65/00* | (2006.01) | |
| *H05B 33/14* | (2006.01) | |
| *C08G 61/12* | (2006.01) | |
| *H05B 33/20* | (2006.01) | |
| *C07C 13/28* | (2006.01) | |
| *C07C 13/48* | (2006.01) | |
| *C07C 15/107* | (2006.01) | |
| *C07C 15/02* | (2006.01) | |
| *C09K 11/02* | (2006.01) | |
| *H01L 51/50* | (2006.01) | |

(52) U.S. Cl.
CPC ......... *H01L 51/0007* (2013.01); *C07C 13/28* (2013.01); *C07C 13/48* (2013.01); *C07C 15/02* (2013.01); *C07C 15/107* (2013.01); *C08G 61/12* (2013.01); *C08K 5/01* (2013.01); *C08K 5/06* (2013.01); *C08L 65/00* (2013.01); *C09K 11/02* (2013.01); *C09K 11/06* (2013.01); *H05B 33/14* (2013.01); *H05B 33/20* (2013.01); *C08G 2261/148* (2013.01); *C08G 2261/228* (2013.01); *C08G 2261/312* (2013.01); *C08G 2261/3142* (2013.01); *C08G 2261/3162* (2013.01); *C08G 2261/5222* (2013.01); *C08G 2261/95* (2013.01); *C09K 2211/1029* (2013.01); *C09K 2211/185* (2013.01); *H01L 51/0005* (2013.01); *H01L 51/0039* (2013.01); *H01L 51/0043* (2013.01); *H01L 51/0085* (2013.01); *H01L 51/5016* (2013.01)

(58) Field of Classification Search
CPC ............ H01L 51/0007; H01L 51/0043; H01L 51/0005; H01L 51/0039; H01L 51/0085; H01L 51/5016; H05B 33/20; H05B 33/14; C08L 65/00; C07C 15/02; C07C 13/48; C07C 13/28; C07C 15/107; C09K 11/02; C09K 11/06; C09K 2211/1029; C09K 2211/185; C08K 5/01; C08K 5/06
See application file for complete search history.

(56) References Cited

U.S. PATENT DOCUMENTS

| | | | |
|---|---|---|---|
| 6,878,312 B1 | 4/2005 | Kanbe et al. | |
| 9,045,613 B2 * | 6/2015 | Suzuki | C08K 5/0008 |
| 2004/0225056 A1 | 11/2004 | Spreitzer et al. | |
| 2006/0045959 A1 | 3/2006 | Yasukawa et al. | |
| 2007/0173578 A1 | 7/2007 | Spreitzer et al. | |
| 2009/0103284 A1 * | 4/2009 | Suzuki | C08K 5/0008 362/97.3 |

(Continued)

FOREIGN PATENT DOCUMENTS

| | | |
|---|---|---|
| JP | 2003-308969 A | 10/2003 |
| JP | 2004-031077 A | 1/2004 |

(Continued)

OTHER PUBLICATIONS

Communication dated Jun. 28, 2018, issued by the State Intellectual Property Office of the P.R.C. in corresponding Chinese Application No. 201680012355.X.

(Continued)

Primary Examiner — Alexander C Kollias
(74) Attorney, Agent, or Firm — Sughrue Mion, PLLC

(57) ABSTRACT

A composition comprising an organic EL material, a solvent (A) represented by the formula (1), an aromatic hydrocarbon solvent (B) and an aromatic ether solvent (C):

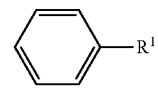

(1)

[wherein $R^1$ represents an alkyl group having a number of carbon atoms of 10 to 12].

8 Claims, 2 Drawing Sheets

(56) References Cited

U.S. PATENT DOCUMENTS

| | | | |
|---|---|---|---|
| 2011/0008590 A1* | 1/2011 | Goddard | H01L 51/0005 428/195.1 |
| 2014/0335639 A1 | 11/2014 | Takashige | |
| 2015/0228901 A1 | 8/2015 | Suzuki et al. | |
| 2015/0270485 A1* | 9/2015 | Watanabe | H01L 51/0007 257/40 |

FOREIGN PATENT DOCUMENTS

| | | |
|---|---|---|
| JP | 2004-535653 A | 11/2004 |
| JP | 2006-066294 A | 3/2006 |
| JP | 2006-348288 A | 12/2006 |
| JP | 2007-527624 A | 9/2007 |
| JP | 2011-042794 A | 3/2011 |
| JP | 2011-517369 A | 6/2011 |
| JP | 2012-039083 A | 2/2012 |
| JP | 2013-026164 A | 2/2013 |
| JP | 2015-185640 A | 10/2015 |
| WO | 2013/088744 A1 | 6/2013 |

OTHER PUBLICATIONS

International Search Report for PCT/JP2016/056167 dated May 31, 2016 [PCT/ISA/210].
Written Opinion for PCT/JP2016/056167 dated May 31, 2016 [PCT/ISA/237].
Second Office Action dated May 21, 2019 in Chinese Patent Application No. 201680012355.X with translation.

\* cited by examiner

[Fig. 1]
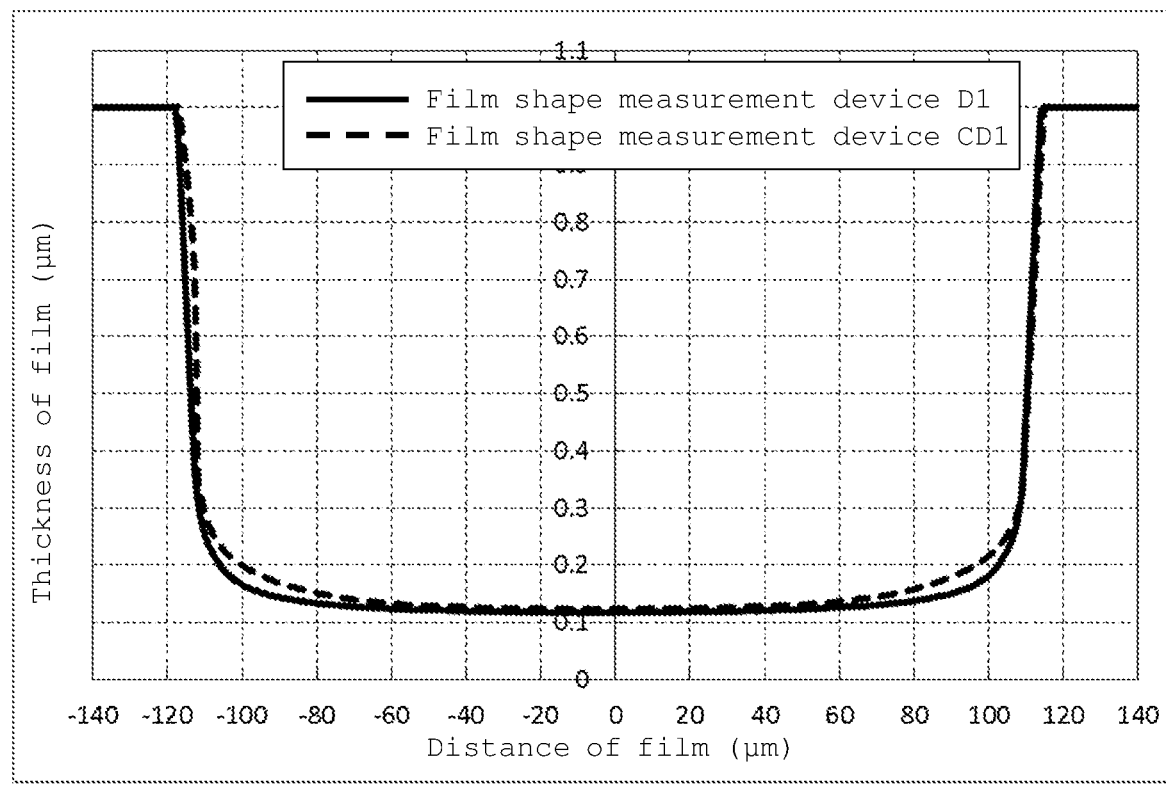

[Fig. 2]
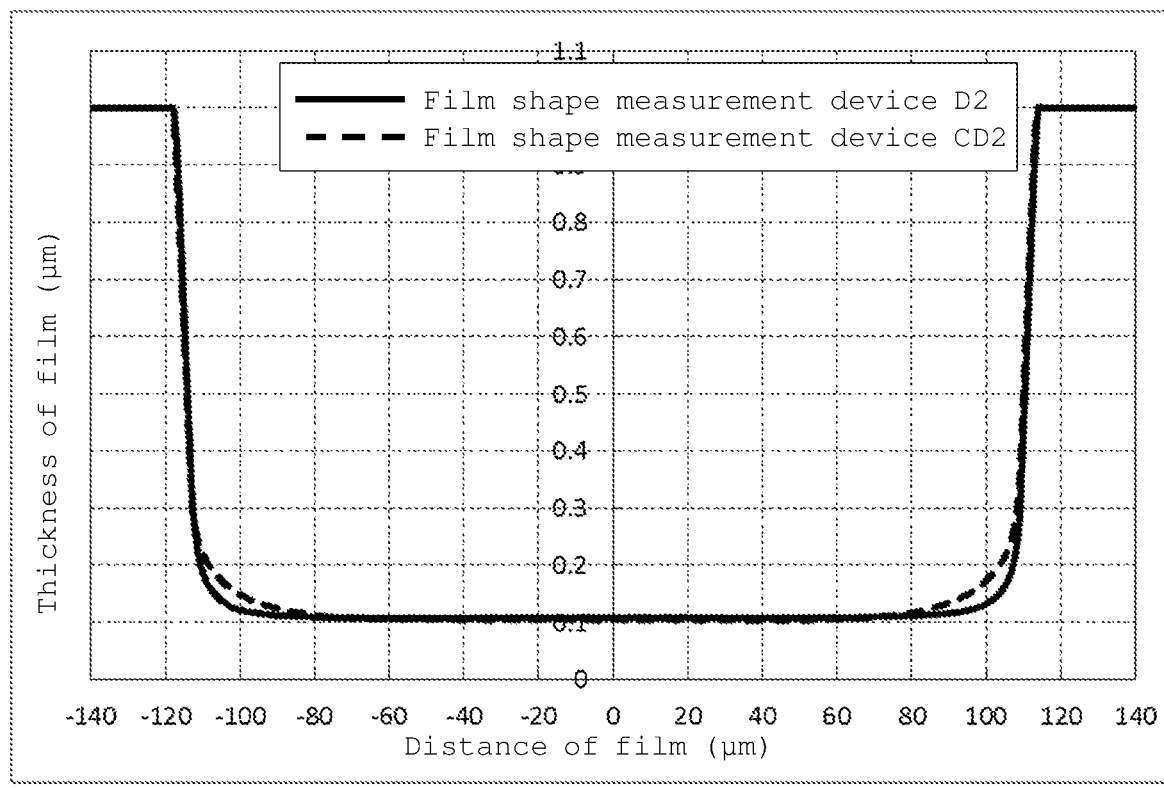

COMPOSITION AND LIGHT EMITTING DEVICE USING THE SAME

CROSS REFERENCE TO RELATED APPLICATIONS

This application is a National Stage of International Application No. PCT/JP2016/056167 filed Mar. 1, 2016, claiming priority based on Japanese Patent Application No. 2015-043254 filed Mar. 5, 2015, the contents of all of which are incorporated herein by reference in their entirety.

TECHNICAL FIELD

The present invention relates to a composition and a light emitting device using the same.

BACKGROUND ART

An organic electroluminescent device (hereinafter, referred to also as "light emitting device") can be suitably used in applications such as display and illumination because of high light emission efficiency and low driving voltage. This light emitting device has organic layers such as a light emitting layer, a charge transporting layer and the like. An organic layer can be formed by using discharge type application methods typified by an inkjet printing method, by using a composition containing a soluble organic electroluminescent material (hereinafter, referred to also as "organic EL material") and a solvent. By forming an organic layer using a discharge type application method, a large-area light emitting device can be produced by a simple process. For this reason, a composition containing a soluble organic EL material and a solvent is investigated.

In Patent document 1, compositions containing soluble an organic EL materials (specifically, polymer organic EL material), aromatic hydrocarbon solvents (specifically, cyclohexylbenzene) and aromatic ether solvents (specifically, 4-methylanisole) are suggested, as the composition used in an inkjet printing method. Patent document 1 does not describe a combination of these solvents with a solvent (A) represented by the formula (1) described later.

PRIOR ART DOCUMENT

Patent Document

[Patent Document 1] Japanese Patent Application National Publication No. 2013-026164

SUMMARY OF THE INVENTION

A film formed by a discharge type application method using the above-described composition has not necessarily sufficient flatness.

The present invention has an object of providing a composition containing an organic EL material and a solvent which is useful for production of a film excellent in flatness when used in a discharge type application method. Further, the present invention has an object of providing a light emitting device having a film formed by using the composition.

The present invention is as described below.
[1] A composition comprising
an organic EL material,
a solvent (A) represented by the formula (1),
an aromatic hydrocarbon solvent (B) and
an aromatic ether solvent (C):

[Chemical Formula 1]

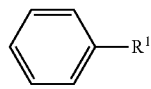

(1)

[wherein $R^1$ represents an alkyl group having a number of carbon atoms of 10 to 12].

[2] The composition according to [1], wherein $R^1$ is an alkyl group having a number of carbon atoms of 10.

[3] The composition according to [1] or [2], wherein the aromatic hydrocarbon solvent (B) is pentylbenzene, hexylbenzene, heptylbenzene, octylbenzene, nonylbenzene, cyclohexylbenzene or tetralin.

[4] The composition according to any one of [1] to [3], wherein the aromatic ether solvent (C) is methylanisole, dimethylanisole, ethylanisole, butyl phenyl ether, butylanisole, pentylanisole, hexylanisole, heptylanisole, octylanisole or phenoxytoluene.

[5] The composition according to any one of [1] to [4], wherein the content of the solvent (A): wtA (by weight), the content of the aromatic hydrocarbon solvent (B): wtB (by weight) and the content of the aromatic ether solvent (C): wtC (by weight) satisfy the formula (1-1):

$$0.05 \leq wtA/(wtA+wtB+wtC) \leq 0.50 \tag{1-1}.$$

[6] The composition according to any one of [1] to [5], wherein the organic EL material is a polymer compound containing at least one constitutional unit selected from the group consisting of a constitutional unit represented by the formula (X) and a constitutional unit represented by the formula (Y):

[Chemical Formula 2]

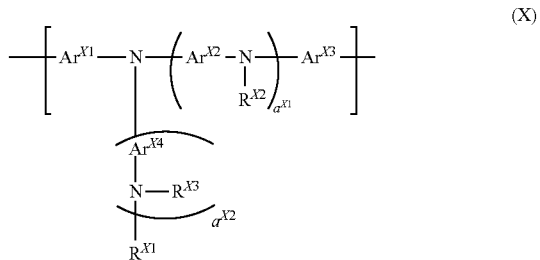

(X)

[wherein,
$a^{X1}$ and $a^{X2}$ each independently represent an integer of 0 or more.
$Ar^{X1}$ and $Ar^{X3}$ each independently represent an arylene group or a divalent heterocyclic group, and the forgoing groups optionally have a substituent.
$Ar^{X2}$ and $Ar^{X4}$ each independently represent an arylene group, a divalent heterocyclic group or a divalent group in which at least one arylene group and at least one divalent heterocyclic group are bonded directly, and the forgoing groups optionally have a substituent. When a plurality of $Ar^{X2}$ and $Ar^{X4}$ are present, they may be the same or different at each occurrence.
$R^X$, $R^{X2}$ and $R^{X3}$ each independently represent a hydrogen atom, an alkyl group, a cycloalkyl group, an aryl group or a monovalent heterocyclic group, and the forgoing groups optionally have a substituent. When a plurality of $R^{X2}$ and $R^{X3}$ are present, they may be the same or different at each occurrence.]

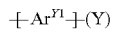   [Chemical Formula 3]

[wherein $Ar^{Y1}$ represents an arylene group, a divalent heterocyclic group or a divalent group in which at least one arylene group and at least one divalent heterocyclic group are bonded directly, and the forgoing groups optionally have a substituent].

[7] The composition according to any one of [1] to [5], wherein the organic EL material is an iridium complex.

[8] The composition according to [7], wherein the iridium complex is an iridium complex represented by the formula (Ir-1), an iridium complex represented by the formula (Ir-2), an iridium complex represented by the formula (Ir-3), an iridium complex represented by the formula (Ir-4) or an iridium complex represented by the formula (Ir-5):

[Chemical Formula 4]

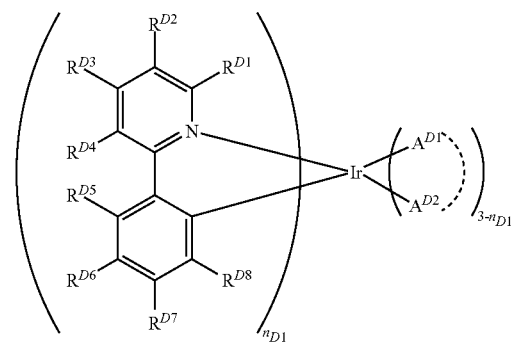

[Chemical Formula 5]

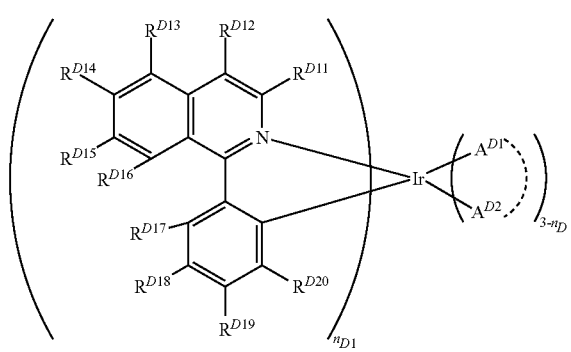

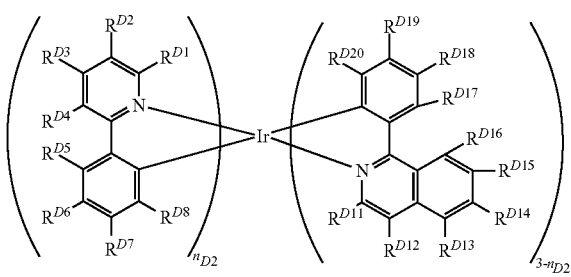

[Chemical Formula 6]

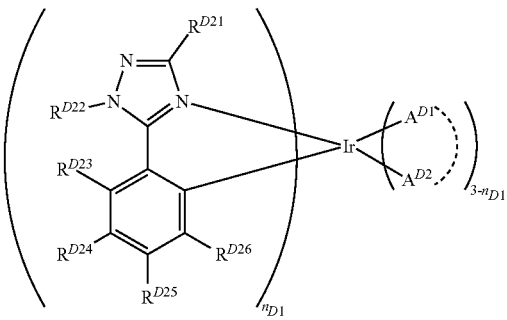

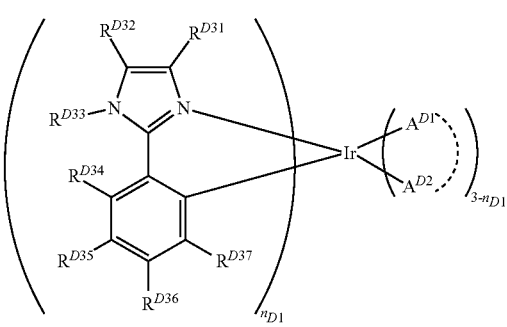

[wherein $n_{D1}$ represents 1, 2 or 3. $n_{D2}$ represents 1 or 2.

$R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$ and $R^{D37}$ each independently represent a hydrogen atom, an alkyl group, a cycloalkyl group, an alkoxy group, a cycloalkoxy group, an aryl group, an aryloxy group, a monovalent heterocyclic group or a halogen atom, and the forgoing groups optionally have a substituent. When a plurality of $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$ and $R^{D37}$ are present, they may be the same or different at each occurrence.

$-A^{D1}$---$A^{D2}$- represents an anionic bidentate ligand. $A^{D1}$ and $A^{D2}$ each independently represent a carbon atom, an oxygen atom or a nitrogen atom bonding to an iridium atom, and these atoms may be ring constituent atoms. When a plurality of $-A^{D1}$---$A^{D2}$- are present, they may be the same or different].

[9] A light emitting device comprising a film formed by using the composition according to any one of [1] to [8].

BRIEF EXPLANATION OF DRAWINGS

FIG. 1 shows the results of measurement of film shape in a film shape measurement device D1 (Example D1) and a film shape measurement device CD1 (Comparative Example CD1).

FIG. 2 shows the results of measurement of film shape in a film shape measurement device D2 (Example D2) and a film shape measurement device CD2 (Comparative Example CD2).

MODES FOR CARRYING OUT THE INVENTION

Suitable embodiments of the present invention will be illustrated in detail below.

Explanation of Common Term

Terms commonly used in the present specification have the following meanings unless otherwise stated.

Me represents a methyl group, Et represents an ethyl group, Bu represents a butyl group, i-Pr represents an isopropyl group and t-Bu represents a tert-butyl group.

The hydrogen atom may be a heavy hydrogen atom or a light hydrogen atom.

In the formula representing a metal complex, a solid line representing a bond to the central metal denotes a covalent bond or a coordinate bond.

"Polymer compound" denotes a polymer having molecular weight distribution and having a polystyrene-equivalent number-average molecular weight of $1 \times 10^3$ to $1 \times 10^8$.

The polymer compound may be any of a block copolymer, a random copolymer, an alternate copolymer and a graft copolymer, and may also be in other embodiments.

If a polymerization active group remains intact at the end group of a polymer compound, the light emitting property or luminance life may possibly lower in the case of use of the polymer compound for fabrication of a light emitting device, thus, it is preferable that the end group is a stable group. This end group is preferably a group having a conjugated bond to the main chain, and includes, for example, groups bonding to an aryl group or a monovalent heterocyclic group via a carbon-carbon bond.

"Low molecular weight compound" denotes a compound having no molecular weight distribution and having a molecular weight of $1 \times 10^4$ or less.

"Constitutional unit" denotes a unit occurring one or more times in a polymer compound.

"Alkyl group" may be any of linear and branched. The linear alkyl group has a number of carbon atoms of usually 1 to 50, preferably 3 to 30, more preferably 4 to 20, not including the number of carbon atoms of the substituent. The branched alkyl group has a number of carbon atoms of usually 3 to 50, preferably 3 to 30, more preferably 4 to 20, not including the number of carbon atoms of the substituent.

The alkyl group optionally has a substituent, and examples thereof include a methyl group, an ethyl group, a propyl group, an isopropyl group, a butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group and a dodecyl group, and groups obtained by substituting a hydrogen atom of these groups with a cycloalkyl group, an alkoxy group, a cycloalkoxy group, an aryl group, a fluorine atom and the like, and examples thereof include a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl) propyl group and a 6-ethyloxyhexyl group.

"Cycloalkyl group" has a number of carbon atoms of usually 3 to 50, preferably 3 to 30, more preferably 4 to 20, not including the number of carbon atoms of the substituent.

The cycloalkyl group optionally has a substituent, and examples thereof include a cyclohexyl group, a cyclohexylmethyl group and a cyclohexylethyl group.

"Aryl group" denotes an atomic group remaining after removing from an aromatic hydrocarbon one hydrogen atom bonding directly to a carbon atom constituting the ring. The aryl group has a number of carbon atoms of usually 6 to 60, preferably 6 to 20, more preferably 6 to 10, not including the number of carbon atoms of the substituent.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group and a 4-phenylphenyl group, and groups obtained by substituting a hydrogen atom of these groups with an alkyl group, a cycloalkyl group, an alkoxy group, a cycloalkoxy group, an aryl group, a fluorine atom and the like.

"Alkoxy group" may be any of linear and branched. The linear alkoxy group has a number of carbon atoms of usually 1 to 40, preferably 4 to 10, not including the number of carbon atoms of the substituent. The branched alkoxy group has a number of carbon atoms of usually 3 to 40, preferably 4 to 10, not including the number of carbon atoms of the substituent.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group and a lauryloxy group, and groups obtained by substituting a hydrogen atom of these groups with a cycloalkyl group, an alkoxy group, a cycloalkoxy group, an aryl group, a fluorine atom and the like.

"Cycloalkoxy group" has a number of carbon atoms of usually 3 to 40, preferably 4 to 10, not including the number of carbon atoms of the substituent.

The cycloalkoxy group optionally has a substituent, and examples thereof include a cyclohexyloxy group.

"Aryloxy group" has a number of carbon atoms of usually 6 to 60, preferably 6 to 48, not including the number of carbon atoms of the substituent.

The aryloxy group optionally has a substituent, and examples thereof include a phenoxy group, a 1-naphthyloxy group, a 2-naphthyloxy group, a 1-anthracenyloxy group, a 9-anthracenyloxy group and a 1-pyrenyloxy group, and groups obtained by substituting a hydrogen atom of these groups with an alkyl group, a cycloalkyl group, an alkoxy group, a cycloalkoxy group, a fluorine atom and the like.

"p-Valent heterocyclic group" (p represents an integer of 1 or more.) denotes an atomic group remaining after removing from a heterocyclic compound P hydrogen atoms among hydrogen atoms bonding directly to carbon atoms or hetero atoms constituting the ring. Of p-valent heterocyclic groups, preferable are "p-valent aromatic heterocyclic groups" as an atomic group remaining after removing from an aromatic heterocyclic compound p hydrogen atoms among hydrogen atoms bonding directly to carbon atoms or hetero atoms constituting the ring.

"Aromatic heterocyclic compound" includes, for example, compounds in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzophosphole and the like, and compounds in which an aromatic ring is condensed to a heterocyclic ring even if the heterocyclic ring itself shows no aromaticity such as phenoxazine, phenothiazine, dibenzoborole, dibenzosilole, benzopyran and the like.

The monovalent heterocyclic group has a number of carbon atoms of usually 2 to 60, preferably 4 to 20, not including the number of carbon atoms of the substituent.

The monovalent heterocyclic group optionally has a substituent, and examples thereof include a thienyl group, a pyrrolyl group, a furyl group, a pyridyl group, a piperidinyl group, a quinolinyl group, an isoquinolinyl group, a pyrimidinyl group and a triazinyl group, and groups obtained by substituting a hydrogen atom of these groups with an alkyl group, a cycloalkyl group, an alkoxy group, a cycloalkoxy group and the like.

"Halogen atom" denotes a fluorine atom, a chlorine atom, a bromine atom or an iodine atom.

"Amino group" optionally has a substituent, and a substituted amino group is preferable. As the substituent which the amino group has, an alkyl group, a cycloalkyl group, an aryl group or a monovalent heterocyclic group is preferable.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl)amino group and a bis(3,5-di-tert-butylphenyl)amino group.

"Alkenyl group" may be any of linear and branched. The linear alkenyl group has a number of carbon atoms of usually 2 to 30, preferably 3 to 20, not including the number of carbon atoms of the substituent. The branched alkenyl group has a number of carbon atoms of usually 3 to 30, preferably 4 to 20, not including the number of carbon atoms of the substituent.

"Cycloalkenyl group" has a number of carbon atoms of usually 3 to 30, preferably 4 to 20, not including the number of carbon atoms of the substituent.

The alkenyl group and the cycloalkenyl group optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group and a 7-octenyl group, and these groups having a substituent.

"Alkynyl group" may be any of linear and branched. The alkynyl group has a number of carbon atoms of usually 2 to 20, preferably 3 to 20, not including carbon atoms of the substituent. The branched alkynyl group has a number of carbon atoms of usually 4 to 30, preferably 4 to 20, not including carbon atoms of the substituent.

"Cycloalkynyl group" has a number of carbon atoms of usually 4 to 30, preferably 4 to 20, not including carbon atoms of the substituent.

The alkynyl group and the cycloalkynyl group optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group and a 5-hexynyl group, and these groups having a substituent.

"Arylene group" denotes an atomic group remaining after removing from an aromatic hydrocarbon two hydrogen atoms bonding directly to a carbon atom constituting the ring. The arylene group has a number of carbon atoms of usually 6 to 60, preferably 6 to 30, more preferably 6 to 18, not including the number of carbon atoms of the substituent.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and these groups having a substituent, preferably, groups represented by the formulae (A-1) to (A-20). The arylene group includes groups obtained by linking a plurality of these groups.

[Chemical Formula 7]

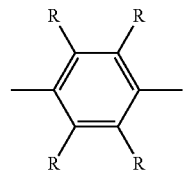
(A-1)

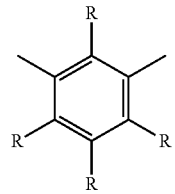
(A-2)

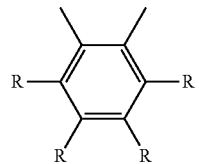
(A-3)

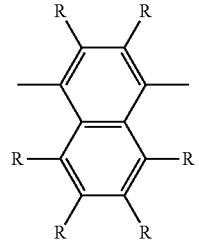
(A-4)

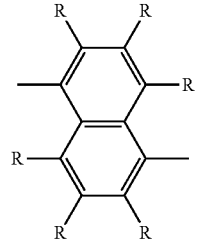
(A-5)

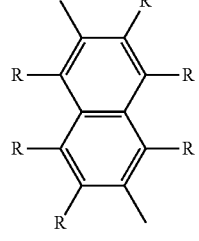
(A-6)

[Chemical Formula 8]
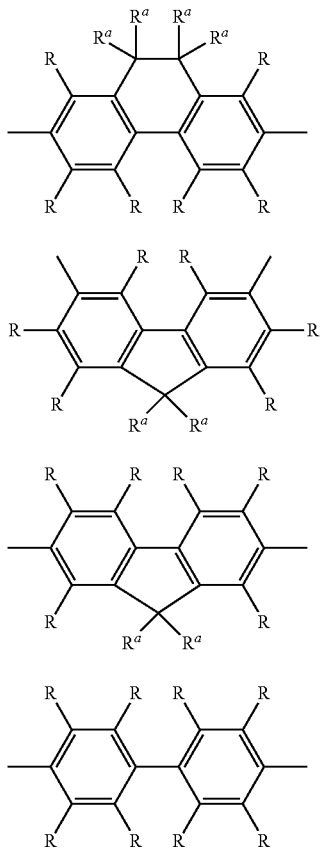
(A-7)
(A-8)
(A-9)
(A-10)
[Chemical Formula 9]
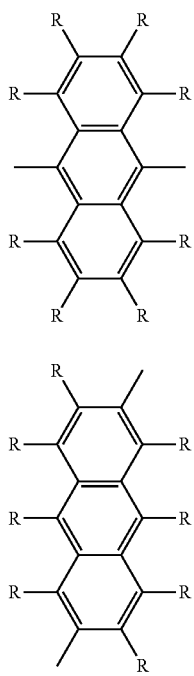
(A-11)
(A-12)
[Chemical Formula 10]
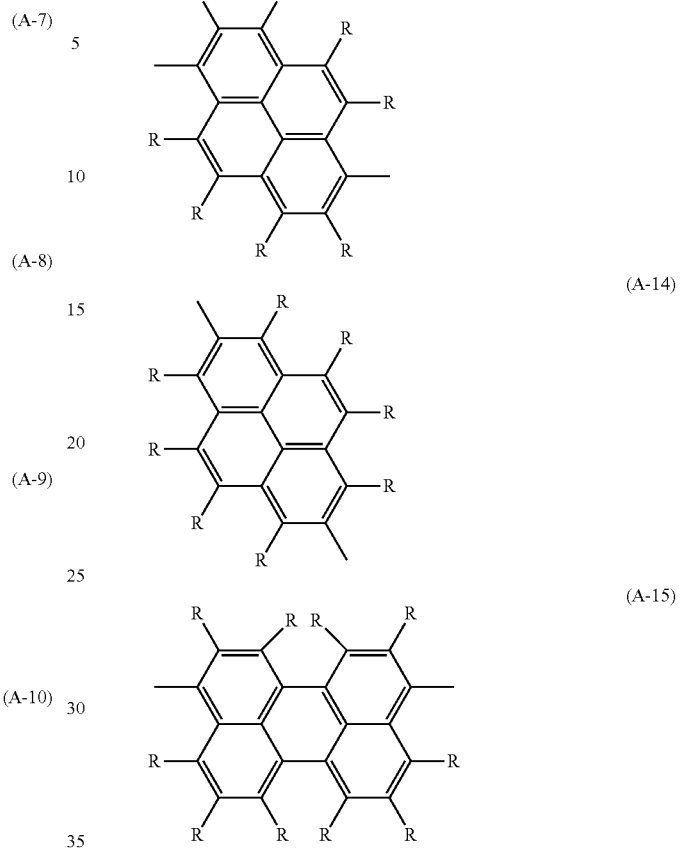
(A-13)
(A-14)
(A-15)
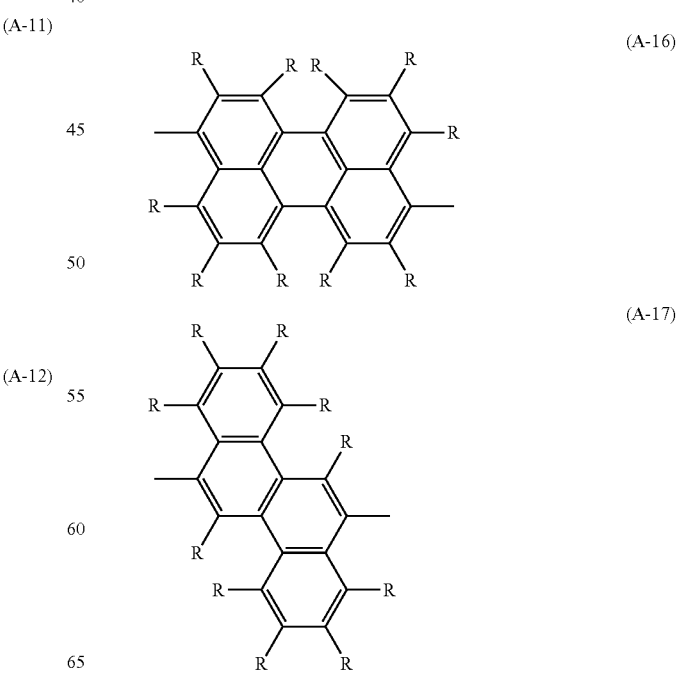
(A-16)
(A-17)

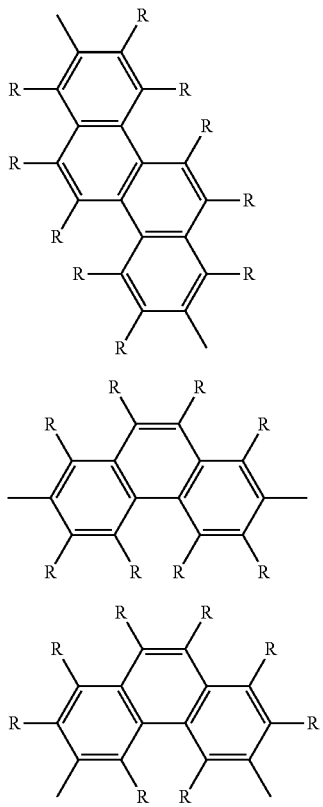

(A-18)

(A-19)

(A-20)

[wherein R and R$^a$ each independently represent a hydrogen atom, an alkyl group, a cycloalkyl group, an aryl group or a mono-valent heterocyclic group. A plurality of R and R$^a$ each may be the same or different, and the plurality of R$^a$ may be combined together to form a ring together with atoms to which they are linked].

The divalent heterocyclic group has a number of carbon atoms of usually 2 to 60, preferably 3 to 20, more preferably 4 to 15, not including the number of carbon atoms of the substituent. The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of these groups.

[Chemical Formula 11]

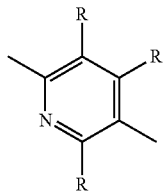

(AA-1)

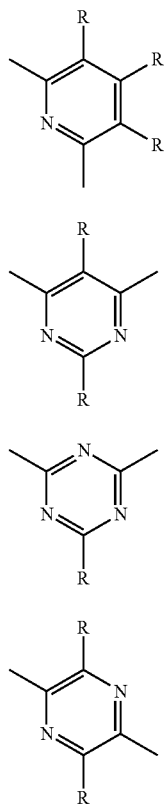

(AA-2)

(AA-3)

(AA-4)

(AA-5)

(AA-6)

(AA-7)

[Chemical Formula 12]

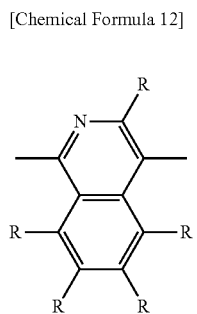

(AA-8)

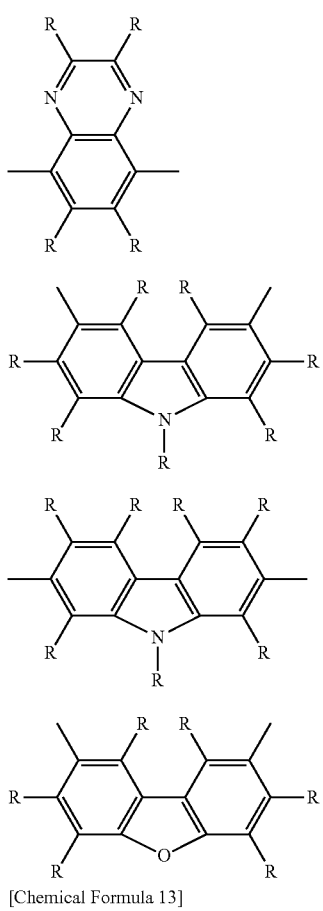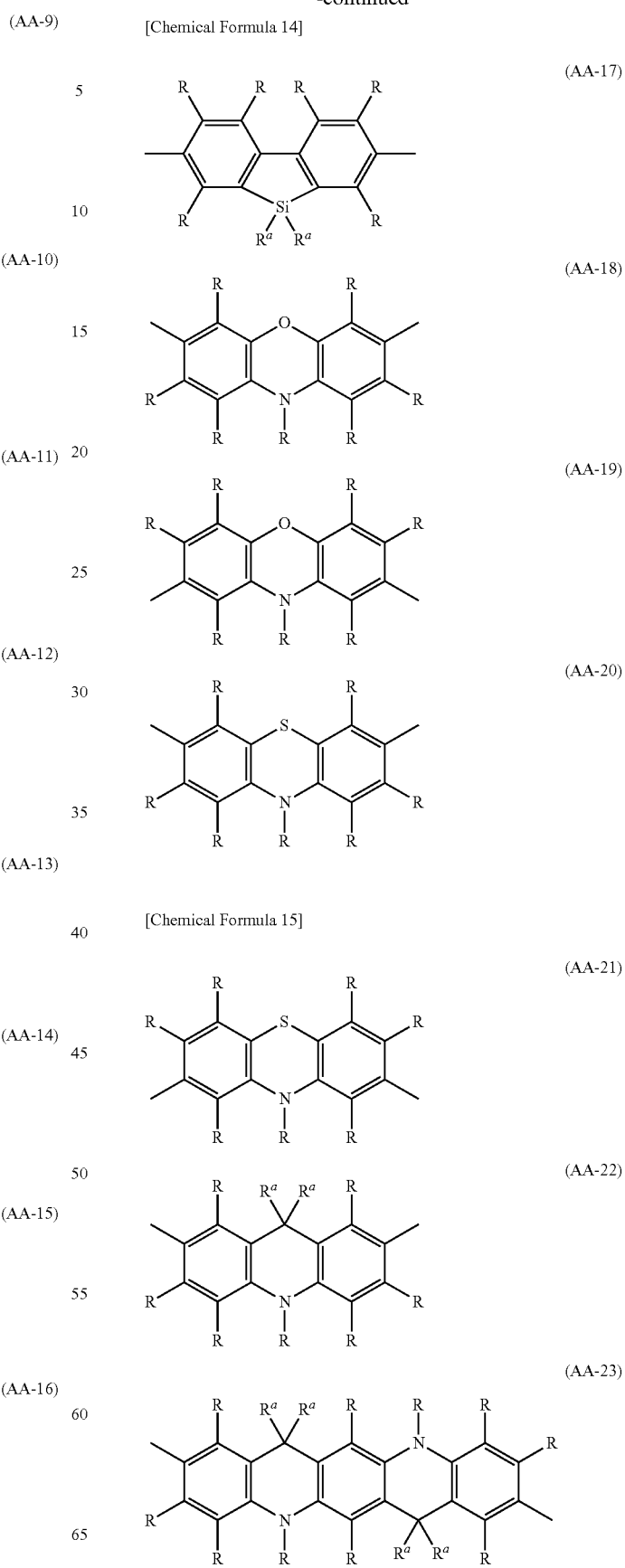

-continued (AA-24) 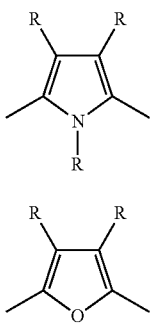

(AA-25)

(AA-26) 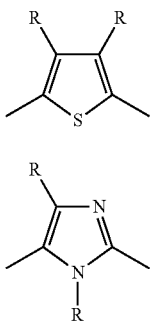

(AA-27)

(AA-28)

(AA-29) 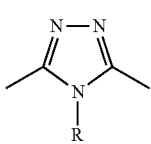

(AA-30)

(AA-31) 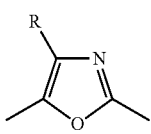

(AA-32)

(AA-33) 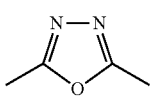

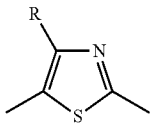

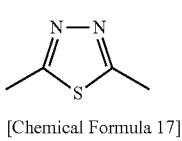

(AA-34) 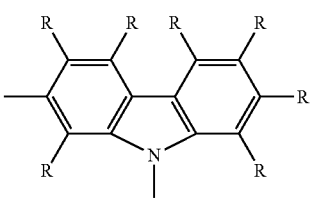

[wherein R and $R^a$ represent the same meaning as described above.]

"Crosslink group" is a group capable of generating a novel bond by subjecting to a heating treatment, an ultraviolet irradiation treatment, a near-ultraviolet irradiation treatment, a visible light irradiation treatment, an infrared irradiation treatment, a radical reaction and the like, and is preferably a group represented by any one of the formulae (B-1)-(B-17). The foregoing groups optionally have a substituent.

[Chemical Formula 18]

(B-1) 

(B-2) 

(B-3) 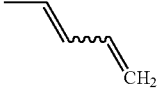

(B-4) 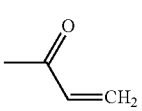

(B-5) 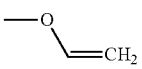

(B-6) 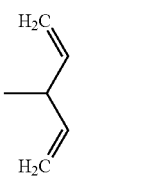

(B-7) 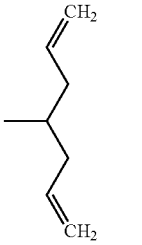

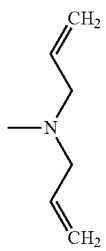 (B-8)

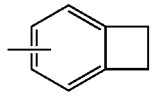 (B-9)

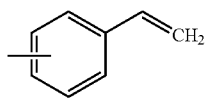 (B-10)

 (B-11)

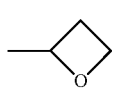 (B-12)

 (B-13)

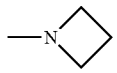 (B-14)

 (B-15)

 (B-16)

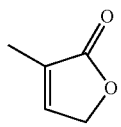 (B-17)

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may also be a crosslink group.

<Solvent>

The solvent (A), the aromatic hydrocarbon solvent (B) and the aromatic ether solvent (C) contained in the composition of the present invention will be illustrated.

[Solvent (A)]

The solvent (A) is a solvent represented by the formula (1).

[Chemical Formula 19]

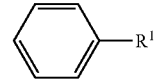 (1)

The alkyl group having a number of carbon atoms of 10 to 12 represented by $R^1$ may be a linear alkyl group or a branched alkyl group, and is preferably a linear alkyl group.

$R^1$ is preferably an alkyl group having a number of carbon atoms of 10, and is preferably a linear alkyl group having a number of carbon atoms of 10.

The alkyl group having a number of carbon atoms of 10 to 12 represented by $R^1$ includes, for example, linear alkyl groups such as a decyl group, an undecyl group, a dodecyl group and the like; and branched alkyl groups such as a methylnonyl group, a methyldecyl group, a methylundecyl group, a dimethyloctyl group, a dimethylnonyl group, a dimethyldecyl group, a trimethylheptyl group, a trimethyloctyl group, a trimethylnonyl group, a tetramethylhexyl group, a tetramethylheptyl group, a tetramethyloctyl group, a pentamethylhexyl group, a pentamethylheptyl group, a hexamethylhexyl group and the like, and preferable is a decyl group, an undecyl group, a dodecyl group, a tetramethyloctyl group, a pentamethylheptyl group or a hexamethylhexyl group, more preferable is a decyl group, an undecyl group or a dodecyl group, further preferable is a 1-decyl group, a 2-decyl group, a 3-decyl group, a 4-decyl group, a 5-decyl group, a 1-undecyl group, a 2-undecyl group, a 3-undecyl group, a 1-dodecyl group, a 2-dodecyl group or a 3-dodecyl group, particularly preferable is a 1-decyl group, a 2-decyl group or a 3-decyl group.

In the composition of the present invention, the solvent (A) may be contained singly or two or more kinds of the solvents may be contained.

[Aromatic Hydrocarbon Solvent (B)]

The aromatic hydrocarbon solvent (B) is an aromatic hydrocarbon solvent different from the solvent (A).

The aromatic hydrocarbon solvent (B) has a total number of carbon atoms of preferably 6 to 15, more preferably 7 to 15.

The aromatic hydrocarbon solvent (B) is preferably one containing one benzene ring, and more preferably a benzene derivative having a total number of carbon atoms of 7 to 15 and substituted with an alkyl group or a cycloalkyl group.

The aromatic hydrocarbon solvent (B) includes, for example, toluene, xylene, trimethylbenzene, ethylbenzene, diethylbenzene, ethylmethylbenzene, propylbenzene, butylbenzene, pentylbenzene, hexylbenzene, heptylbenzene, octylbenzene, nonylbenzene, dipropylbenzene, cyclohexylbenzene and tetralin, and is preferably pentylbenzene, hexylbenzene, heptylbenzene, octylbenzene, nonylbenzene, cyclohexylbenzene or tetralin, more preferably heptylbenzene, octylbenzene, nonylbenzene, cyclohexylbenzene or tetralin, further preferably heptylbenzene, octylbenzene, nonylbenzene or cyclohexylbenzene, particularly preferably 1-heptylbenzene, 1-octylbenzene, 1-nonylbenzene or cyclohexylbenzene, since a film formed by using the composition of the present invention is more excellent in flatness.

In the composition of the present invention, the aromatic hydrocarbon solvent (B) may be contained singly or two or more kinds of the aromatic hydrocarbon solvents may be contained.

[Aromatic Ether Solvent (C)]

The aromatic ether solvent (C) has a total number of carbon atoms of preferably 7 to 15.

The aromatic ether solvent (C) includes alkylaryl ethers having a total number of carbon atoms of 7 to 15 and in which the aryl portion is optionally substituted with an alkyl group and diaryl ethers having a total number of carbon atoms of 12 to 15 and optionally substituted with an alkyl group, and preferable are alkylphenyl ethers having a total number of carbon atoms of 7 to 15 and in which the phenyl portion is optionally substituted with an alkyl group and diphenyl ethers having a total number of carbon atoms of 12 to 15 and optionally substituted with an alkyl group.

The aromatic ether solvent (C) includes, for example, anisole, ethylphenyl ether, methylanisole, dimethylanisole, ethylanisole, butyl phenyl ether, butylanisole, pentylanisole, hexylanisole, heptylanisole, octylanisole, 1-methoxynaphthalene, diphenyl ether and phenoxytoluene, and is preferably methylanisole, dimethylanisole, ethylanisole, butyl phenyl ether, butylanisole, pentylanisole, hexylanisole, heptylanisole, octylanisole or phenoxytoluene, more preferably 2-methylanisole, 3-methylanisole, 4-methylanisole, 2,5-dimethylanisole, 2-ethylanisole, 4-ethylanisole or 3-phenoxytoluene, further preferably 2-methylanisole, 3-methylanisole, 4-methylanisole or 3-phenoxytoluene, since a film formed by using the composition of the present invention is more excellent in flatness.

In the composition of the present invention, the aromatic ether solvent (C) may be contained singly or two or more kinds of the aromatic ether solvents may be contained.

[Composition Ratio of Solvent]

The content of a solvent (A): wtA (by weight), the content of an aromatic hydrocarbon solvent (B): wtB (by weight) and the content of an aromatic ether solvent (C): wtC (by weight), contained in the composition of the present invention, preferably satisfy the formula (1-1), more preferably satisfy the formula (1-2), further preferably satisfy the formula (1-3), since a film formed by using the composition of the present invention is more excellent in flatness.

$$0.05 \leq wtA/(wtA+wtB+wtC) \leq 0.50 \quad (1-1)$$

$$0.10 \leq wtA/(wtA+wtB+wtC) \leq 0.40 \quad (1-2)$$

$$0.15 \leq wtA/(wtA+wtB+wtC) \leq 0.30 \quad (1-3)$$

(When two or more kinds of the solvents (A) are contained in the composition of the present invention, wtA represents the total content (by weight) of the solvents (A), when two or more kinds of the aromatic hydrocarbon solvents (B) are contained, wtB represents the total content (by weight) of the aromatic hydrocarbon solvents (B), and when two or more kinds of the aromatic ether solvents (C) are contained, wtC represents the total content (by weight) of the aromatic ether solvents (C).).

The content of a solvent (A): wtA (by weight), the content of an aromatic hydrocarbon solvent (B): wtB (by weight) and the content of an aromatic ether solvent (C): wtC (by weight), contained in the composition of the present invention, preferably satisfy the formula (2-1), more preferably satisfy the formula (2-2), further preferably satisfy the formula (2-3), since a film formed by using the composition of the present invention is more excellent in flatness.

$$0.50 \leq wtB+wtC/(wtA+wtB+wtC) \leq 0.95 \quad (2-1)$$

$$0.60 \leq wtB+wtC/(wtA+wtB+wtC) \leq 0.90 \quad (2-2)$$

$$0.70 \leq wtB+wtC/(wtA+wtB+wtC) \leq 0.85 \quad (2-3)$$

The content of an aromatic hydrocarbon solvent (B): wtB (by weight) and the content of an aromatic ether solvent (C): wtC (by weight), contained in the composition of the present invention, preferably satisfy the formula (3-1), more preferably satisfy the formula (3-2), further preferably satisfy the formula (3-3), since a film formed by using the composition of the present invention is more excellent in flatness.

$$0.10 \leq wtB/(wtB+wtC) \leq 0.90 \quad (3-1)$$

$$0.25 \leq wtB/(wtB+wtC) \leq 0.75 \quad (3-2)$$

$$0.40 \leq wtB/(wtB+wtC) \leq 0.60 \quad (3-3)$$

[Other Solvent]

The composition of the present invention may also contain a solvent satisfying the formula (4-1) (hereinafter, referred to also as "solvent (D)") as the solvent other than a solvent (A), an aromatic hydrocarbon solvent (B) and an aromatic ether solvent (C).

$$0.00 < wtD/(wtA+wtB+wtC+wtD) \leq 0.50 \quad (4-1)$$

(wherein wtD represents the content (by weight) of the solvent (D). When two or more kinds of the solvents (D) are contained in the composition of the present invention, wtD represents the total content (by weight) of the solvents (D)).

When the solvent (D) is contained in the composition of the present invention, the content of a solvent (A): wtA (by weight), the content of an aromatic hydrocarbon solvent (B): wtB (by weight), the content of an aromatic ether solvent (C): wtC (by weight) and the content of the solvent (D): wtD (by weight) preferably satisfy the formula (4-2), more preferably satisfy the formula (4-3).

$$0.00 < wtD/(wtA+wtB+wtC+wtD) \leq 0.30 \quad (4-2)$$

$$0.00 < wtD/(wtA+wtB+wtC+wtD) \leq 0.10 \quad (4-3).$$

The solvent (D) includes, for example, aliphatic hydrocarbon solvents, monohydric alcohol solvents, polyhydric alcohol solvents, ester solvents, ketone solvents, aliphatic ether solvents, solvents containing a nitrogen atom and solvents containing a sulfur atom.

In the composition of the present invention, the solvent (D) may be contained singly or two or more kinds of the solvents may be contained.

<Organic EL Material>

The organic EL material to be contained in the composition of the present invention will be explained.

The organic EL material is a material having at least one function selected from a light emitting property, hole transportability, hole injectability, electron transportability and electron injectability. The organic EL material may be a low molecular weight compound or a polymer compound, providing that it is soluble in a solvent (A), an aromatic hydrocarbon solvent (B) or an aromatic ether solvent (C).

[Polymer Compound]

The organic EL material is preferably a polymer compound containing at least one constitutional unit selected from the group consisting of a constitutional unit represented by the formula (X) and a constitutional unit represented by the formula (Y), since a light emitting device having a film formed by using the composition of the present invention is excellent in luminance life.

In the composition of the present invention, the polymer compound containing at least one constitutional unit selected from the group consisting of a constitutional unit represented by the formula (X) and a constitutional unit represented by the formula (Y) may be contained singly or two or more kinds of the polymer compounds may be contained.

[Constitutional Unit Represented by the Formula (X)]

[Chemical Formula 20]

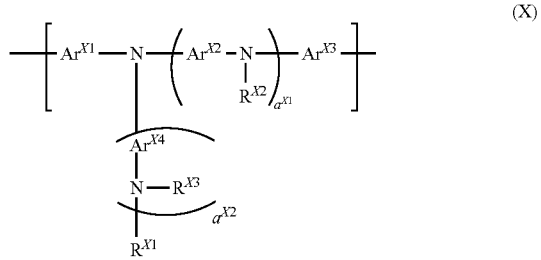

(X)

[wherein
$a^{X1}$ and $a^{X2}$ each independently represent an integer of 0 or more.

$Ar^{X1}$ and $Ar^{X3}$ each independently represent an arylene group or a divalent heterocyclic group, and the forgoing groups optionally have a substituent.

$Ar^{X2}$ and $Ar^{X4}$ each independently represent an arylene group, a divalent heterocyclic group or a divalent group in which at least one arylene group and at least one divalent heterocyclic group are bonded directly, and the forgoing groups optionally have a substituent. When a plurality of $Ar^{X2}$ and $Ar^{X4}$ are present, they may be the same or different at each occurrence.

$R^{X1}$, $R^{X2}$ and $R^{X3}$ each independently represent a hydrogen atom, an alkyl group, a cycloalkyl group, an aryl group or a monovalent heterocyclic group, and the forgoing groups optionally have a substituent. When a plurality of $R^{X2}$ and $R^{X3}$ are present, they may be the same or different at each occurrence].

$a^{X1}$ is preferably an integer of 2 or less, more preferably 1, since a light emitting device having a film formed by using the composition of the present invention is excellent in light emission efficiency.

$a^{X2}$ is preferably an integer of 2 or less, more preferably 0, since a light emitting device having a film formed by using the composition of the present invention is excellent in light emission efficiency.

$R^{X1}$, $R^{X2}$ and $R^{X3}$ represent preferably an alkyl group, a cycloalkyl group, an aryl group or a monovalent heterocyclic group, more preferably an aryl group, and the forgoing groups optionally have a substituent.

The arylene group represented by $Ar^{X1}$ and $Ar^{X3}$ is more preferably a group represented by the formula (A-1) or the formula (A-9), further preferably a group represented by the formula (A-1), and the forgoing groups optionally have a substituent.

The divalent heterocyclic group represented by $Ar^{X1}$ and $Ar^{X3}$ is more preferably a group represented by the formula (AA-1), the formula (AA-2) or the formulae (AA-7)-(AA-26), and the forgoing groups optionally have a substituent.

$Ar^{X1}$ and $Ar^{X3}$ represent preferably an arylene group optionally having a substituent.

The arylene group represented by $Ar^{X2}$ and $Ar^{X4}$ is more preferably a group represented by the formula (A-1), the formula (A-6), the formula (A-7), the formulae (A-9)-(A-11) or the formula (A-19), and the forgoing groups optionally have a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

The more preferable range and the further preferable range of an arylene group and a divalent heterocyclic group in a divalent group in which at least one arylene group and at least one divalent heterocyclic group are bonded directly represented by $Ar^{X2}$ and $Ar^{X4}$ are the same as the more preferable range and the further preferable range of an arylene group and a divalent heterocyclic group represented by $Ar^{X1}$ and $Ar^{X3}$, respectively.

The divalent group in which at least one arylene group and at least one divalent heterocyclic group are bonded directly represented by $Ar^{X2}$ and $Ar^{X4}$ includes, for example, groups represented by the following formulae, and the foregoing groups optionally have a substituent.

[Chemical Formula 21]

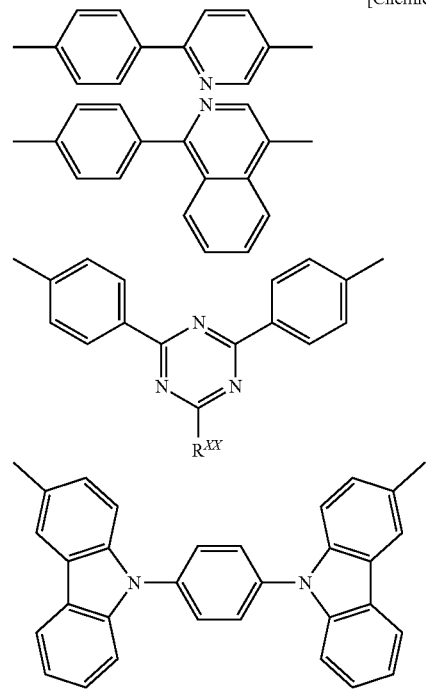

[wherein R represents a hydrogen atom, an alkyl group, a cycloalkyl group, an aryl group or a monovalent heterocyclic group, and the forgoing groups optionally have a substituent].

$R^{XX}$ is preferably an alkyl group, a cycloalkyl group or an aryl group, and the forgoing groups optionally have a substituent.

$Ar^{X2}$ and $Ar^{X4}$ represent preferably an arylene group optionally having a substituent.

The substituent which the group represented by $Ar^{X1}$ to $Ar^{X4}$ and $R^{X1}$ to $R^{X3}$ optionally has is preferably an alkyl group, a cycloalkyl group or an aryl group, and the foregoing groups optionally further have a substituent.

The constitutional unit represented by the formula (X) is preferably a constitutional unit represented by the formulae (X-1)-(X-7), more preferably a constitutional unit represented the formulae (X-1)-(X-6), further preferably a constitutional unit represented the formulae (X-3)-(X-6).

[Chemical Formula 22]

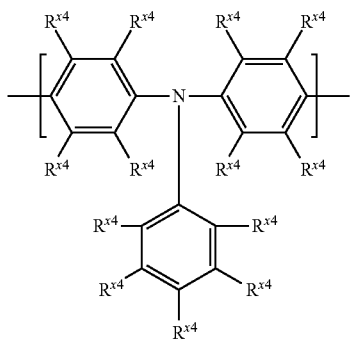
(X-1)

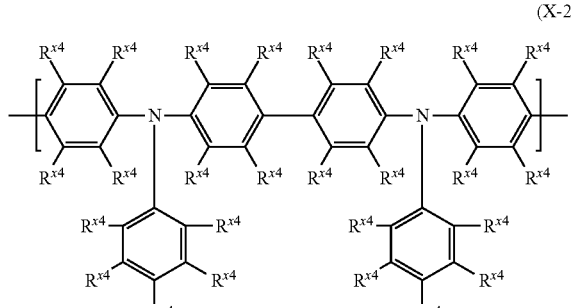
(X-2)

[Chemical Formula 23]

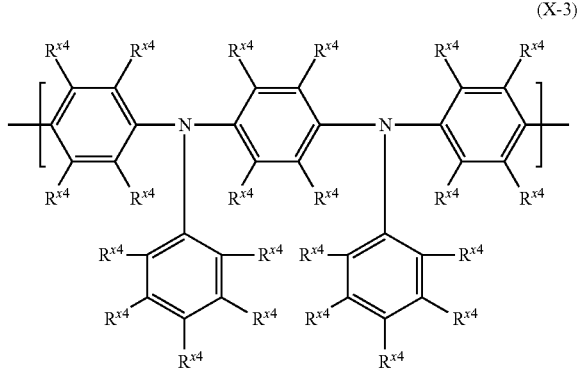
(X-3)

[Chemical Formula 24]

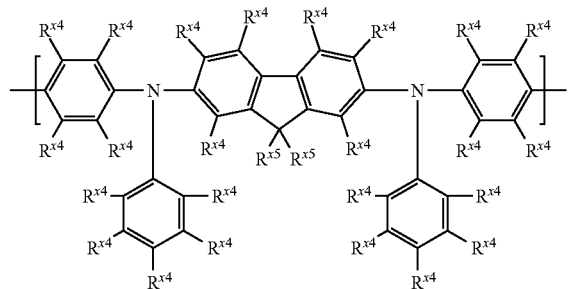
(X-4)

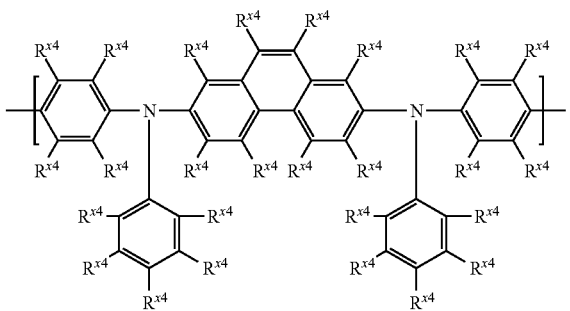
(X-5)

[Chemical Formula 25]

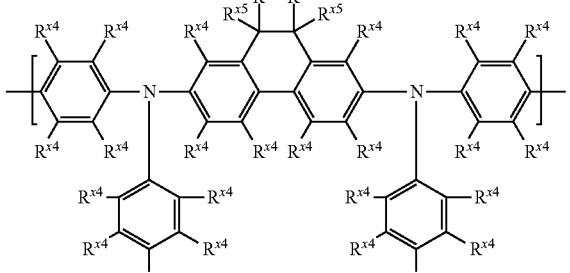
(X-6)

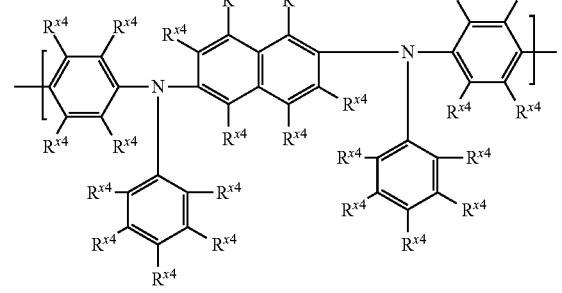
(X-7)

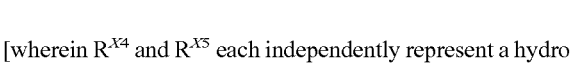

[wherein $R^{X4}$ and $R^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group, and the forgoing groups optionally have a substituent. A plurality of $R^{X4}$ may be the same or different. A plurality of $R^{X5}$ may be the same or different, and adjacent $R^{X5}$ may be combined together to form a ring together with carbon atoms to which they are attached].

The amount of the constitutional unit represented by the formula (X) is preferably 0.1 to 50% by mol, more preferably 1 to 40% by mol, further preferably 5 to 30% by mol with respect to the total amount of constitutional units contained in the polymer compound, since a light emitting device having a film formed by using the composition of the present invention is excellent in hole transportability.

The constitutional unit represented by the formula (X) includes, for example, constitutional units represented by the formulae (X1-1)-(X1-11), and preferable are constitutional units represented by the formulae (X1-3)-(X1-10).

[Chemical Formula 26]
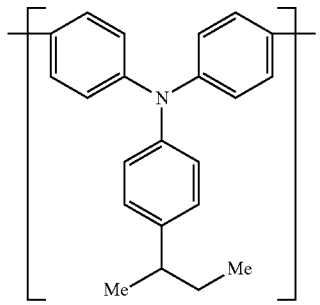
(X1-1)
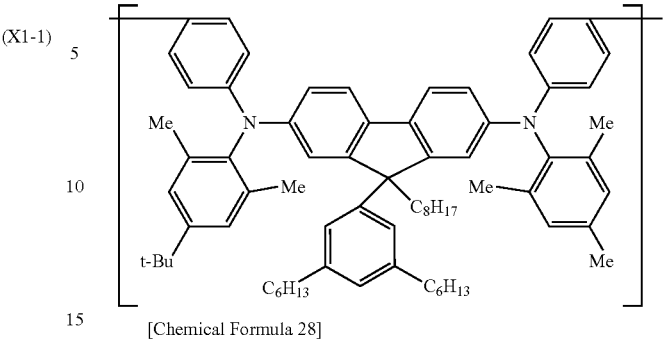
(X1-5)
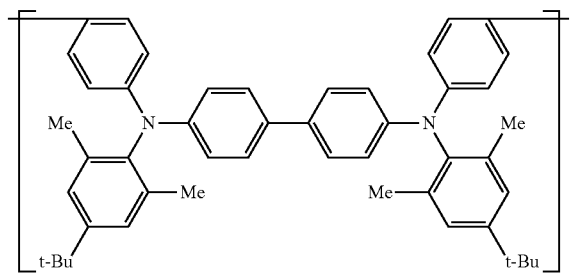
(X1-2)
[Chemical Formula 28]
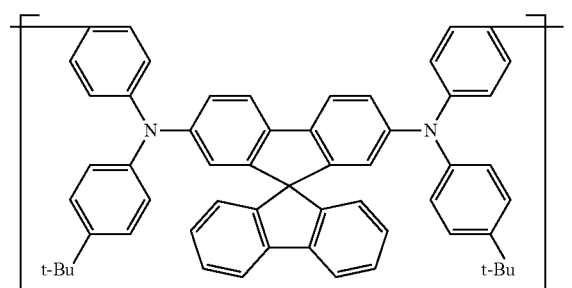
(X1-6)
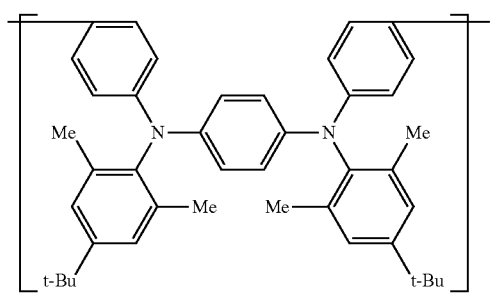
(X1-3)
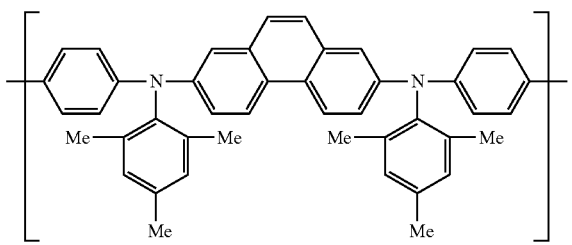
(X1-7)
[Chemical Formula 29]
[Chemical Formula 27]
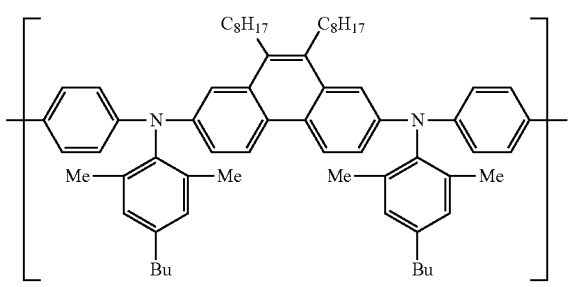
(X1-8)
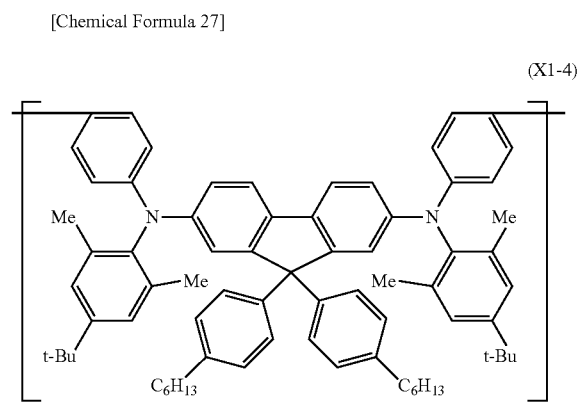
(X1-4)
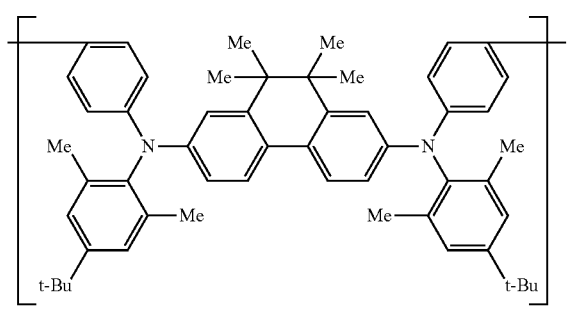
(X1-9)

[Chemical Formula 30]

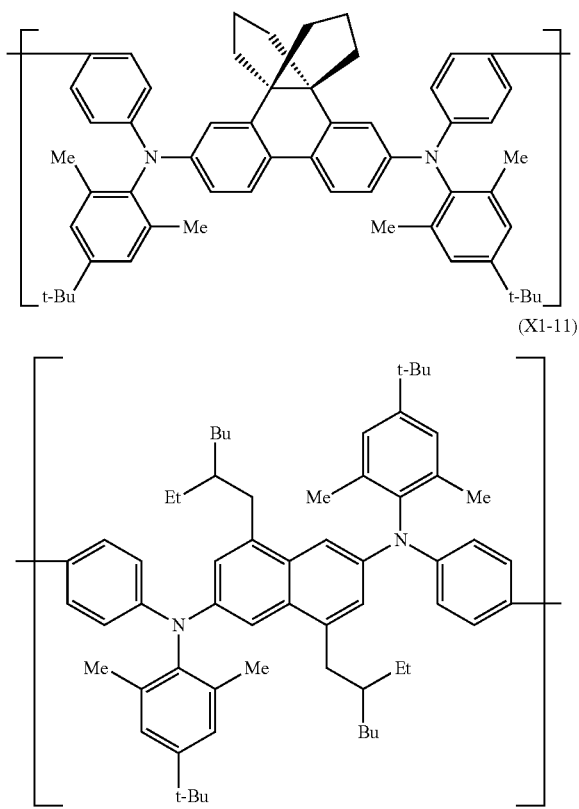

The constitutional unit represented by the formula (X) may be contained singly or two or more kinds of the constitutional units may be contained in the polymer compound.

[Constitutional Unit Represented by the Formula (Y)]

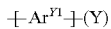 [Chemical Formula 31]

[wherein $Ar^{Y1}$ represents an arylene group, a divalent heterocyclic group or a divalent group in which at least one arylene group and at least one divalent heterocyclic group are bonded directly, and the forgoing groups optionally have a substituent].

The arylene group represented by $Ar^{Y1}$ is more preferably a group represented by the formula (A-1), the formula (A-2), the formula (A-6)-(A-10), the formula (A-19) or the formula (A-20), further preferably a group represented by the formula (A-1), the formula (A-2), the formula (A-7), the formula (A-9) or the formula (A-19), and the forgoing groups optionally have a substituent.

The divalent heterocyclic group represented by $Ar^{Y1}$ is more preferably a group represented by the formula (AA-1)-(AA-4), the formula (AA-10)-(AA-15), the formula (AA-18)-(AA-21), the formula (AA-33) or the formula (AA-34), further preferably a group represented by the formula (AA-4), the formula (AA-10), the formula (AA-12), the formula (AA-14) or the formula (AA-33), and the forgoing groups optionally have a substituent.

The more preferable range and the further preferable range of an arylene group and a divalent heterocyclic group in the divalent group in which at least one arylene group and at least one divalent heterocyclic group are bonded directly represented by $Ar^{Y1}$ are the same as the more preferable range and the further preferable range of an arylene group and a divalent heterocyclic group represented by $Ar^{Y1}$ described above, respectively.

The divalent group in which at least one arylene group and at least one divalent heterocyclic group are bonded directly represented by $Ar^{Y1}$ includes those which are the same as the divalent group in which at least one arylene group and at least one divalent heterocyclic group are bonded directly represented by $Ar^{X2}$ and $Ar^{X4}$ in the formula (X).

The substituent which the group represented by $Ar^{Y1}$ optionally has is preferably an alkyl group, a cycloalkyl group or an aryl group, and the foregoing groups optionally further have a substituent.

The constitutional unit represented by the formula (Y) includes, for example, constitutional units represented by the formulae (Y-1)-(Y-10), and is preferably a constitutional unit represented by the formulae (Y-1)-(Y-3) from the standpoint of the luminance life of a light emitting device having a film formed by using the composition of the present invention, preferably a constitutional unit represented by the formulae (Y-4)-(Y-7) from the standpoint of the electron transportability of a light emitting device having a film formed by using the composition of the present invention, and preferably a constitutional unit represented by the formulae (Y-8)-(Y-10) from the standpoint of the light emission efficiency and hole transportability of a light emitting device having a film formed by using the composition of the present invention.

[Chemical Formula 32]

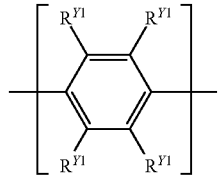
(Y-1)

[wherein $R^{Y1}$ represents a hydrogen atom, an alkyl group, a cycloalkyl group, an alkoxy group, a cycloalkoxy group, an aryl group or a monovalent heterocyclic group, and the forgoing groups optionally have a substituent. A plurality of $R^{Y1}$ may be the same or different, and adjacent $R^{Y1}$ may be combined together to form a ring together with carbon atoms to which they are attached].

$R^{Y1}$ is preferably a hydrogen atom, an alkyl group, a cycloalkyl group or an aryl group, and the forgoing groups optionally have a substituent.

The constitutional unit represented by the formula (Y-1) is preferably a constitutional unit represented by the formula (Y-1').

[Chemical Formula 33]

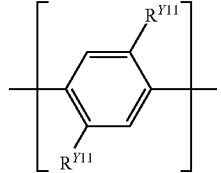
(Y-1')

[wherein $R^{Y11}$ represents an alkyl group, a cycloalkyl group, an alkoxy group, a cycloalkoxy group, an aryl group or a monovalent heterocyclic group, and the forgoing groups optionally have a substituent. A plurality of $R^{Y11}$ may be the same or different].

$R^{Y11}$ is preferably an alkyl group, a cycloalkyl group or an aryl group, more preferably an alkyl group or a cycloalkyl group, and the forgoing groups optionally have a substituent.

[Chemical Formula 34]

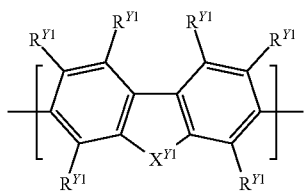

(Y-2)

[wherein $R^{Y1}$ represents the same meaning as described above.

$X^{Y1}$ represents a group represented by $-C(R^{Y2})_2-$, $-C(R^{Y2})=C(R^{Y2})-$ or $C(R^{Y2})_2-C(R^{Y2})_2-$. $R^{Y2}$ represents a hydrogen atom, an alkyl group, a cycloalkyl group, an alkoxy group, a cycloalkoxy group, an aryl group or a monovalent heterocyclic group, and the forgoing groups optionally have a substituent. A plurality of $R^{Y2}$ may be the same or different, and $R^{Y2}$ may be combined together to form a ring together with carbon atoms to which they are attached].

$R^{Y2}$ is preferably an alkyl group, a cycloalkyl group, an aryl group or a monovalent heterocyclic group, more preferably an alkyl group, a cycloalkyl group or an aryl group, and the forgoing groups optionally have a substituent.

The combination of two groups $R^{Y2}$ in the group represented by $-C(R^{Y2})_2-$ in $X^{Y1}$ is preferably one in which both the groups are alkyl groups or cycloalkyl groups, both the groups are aryl groups, both the groups are monovalent heterocyclic groups, or one of them is an alkyl group or a cycloalkyl group and the other is an aryl group or a monovalent heterocyclic group, more preferably one in which one of them is an alkyl group or a cycloalkyl group and the other is an aryl group, and the forgoing groups optionally have a substituent. Two groups $R^{Y2}$ may be combined together to form a ring together with atoms to which they are attached, and when groups $R^{Y2}$ form a ring, the group represented by $-C(R^{Y2})_2-$ is preferably a group represented by the formulae (Y-A1)-(Y-A5), more preferably a group represented by the formula (Y-A4), and the forgoing groups optionally have a substituent.

[Chemical Formula 35]

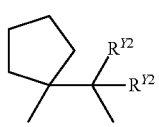

(Y-A1)

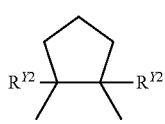

(Y-A2)

(Y-A3)

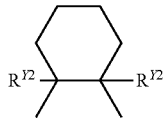

(Y-A4)

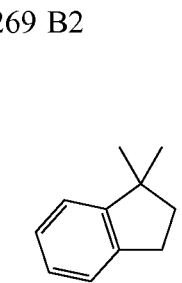

(Y-A5)

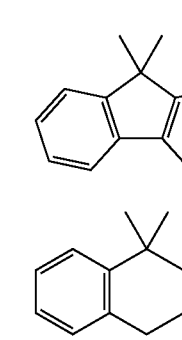

The combination of two groups $R^{Y2}$ in the group represented by $-C(R^{Y2})=C(R^{Y2})-$ in $X^{Y1}$ is preferably one in which both the groups are alkyl groups or cycloalkyl groups, or one of them is an alkyl group or a cycloalkyl group and the other is an aryl group, and the forgoing groups optionally have a substituent.

Four groups $R^{Y2}$ in the group represented by $-C(R^{Y2})_2-C(R^{Y2})_2-$ in $X^{Y1}$ are preferably alkyl groups or cycloalkyl groups optionally having a substituent. A plurality of $R^{Y2}$ may be combined together to form a ring together with atoms to which they are attached, and when groups $R^{Y2}$ form a ring, the group represented by $-C(R^{Y2})_2-C(R^{Y2})_2-$ is preferably a group represented by the formulae (Y-B1)-(Y-B5), more preferably a group represented by the formula (Y-B3), and the forgoing groups optionally have a substituent.

[Chemical Formula 36]

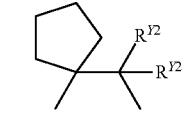

(Y-B1)

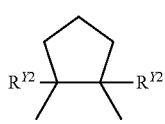

(Y-B2)

(Y-B3)

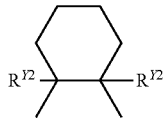

(Y-B4)

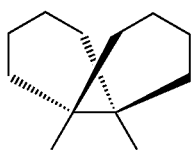
(Y-B5)

[wherein $R^{Y2}$ represents the same meaning as described above].

The constitutional unit represented by the formula (Y-2) is preferably a constitutional unit represented by the formula (Y-2').

[Chemical Formula 37]

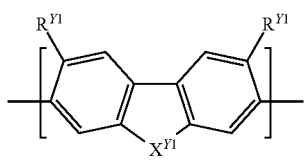
(Y-2')

[wherein $R^{Y1}$ and $X^{Y1}$ represent the same meaning as described above].

[Chemical Formula 38]

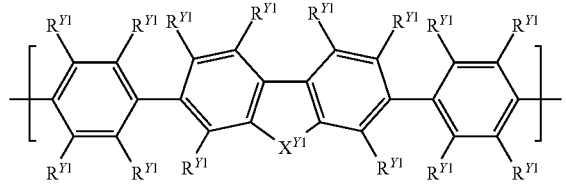
(Y-3)

[wherein $R^{Y1}$ and $X^{Y1}$ represent the same meaning as described above].

The constitutional unit represented by the formula (Y-3) is preferably a constitutional unit represented by the formula (Y-3').

[Chemical Formula 39]

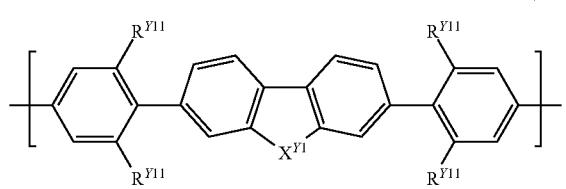
(Y-3')

[wherein $R^{Y11}$ and $X^{Y1}$ represent the same meaning as described above.].

[Chemical Formula 40]

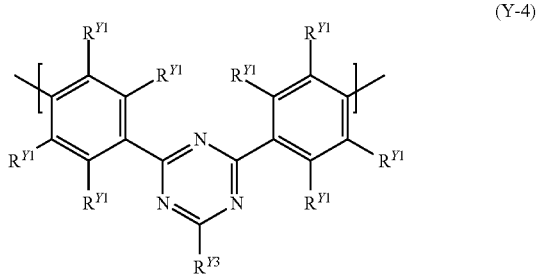
(Y-4)

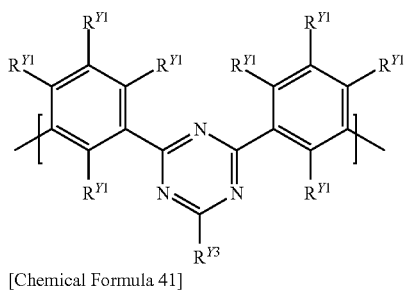
(Y-5)

[Chemical Formula 41]

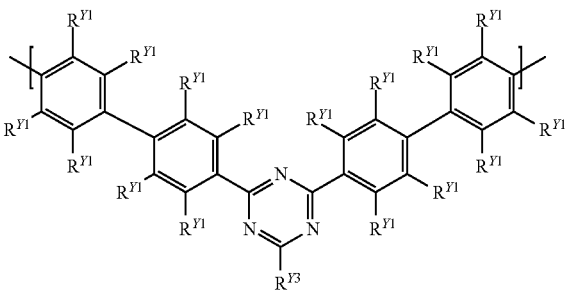
(Y-6)

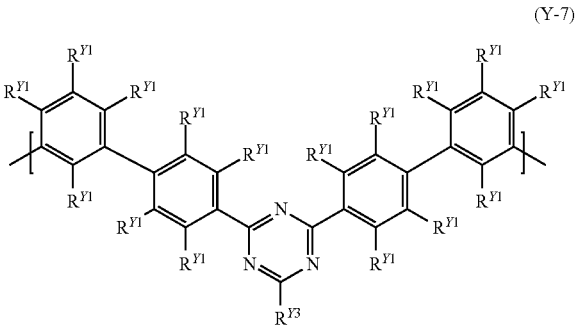
(Y-7)

[wherein $R^{Y1}$ represents the same meaning as described above.

$R^{Y3}$ represents a hydrogen atom, an alkyl group, a cycloalkyl group, an alkoxy group, a cycloalkoxy group, an aryl group or a monovalent heterocyclic group, and the forgoing groups optionally have a substituent].

$R^{Y3}$ is preferably an alkyl group, a cycloalkyl group, an alkoxy group, a cycloalkoxy group, an aryl group or a monovalent heterocyclic group, more preferably an aryl group, and the forgoing groups optionally have a substituent.

The constitutional unit represented by the formula (Y-4) is preferably a constitutional unit represented by the formula (Y-4'), and the constitutional unit represented by the formula (Y-6) is preferably a constitutional unit represented by the formula (Y-6').

[Chemical Formula 42]

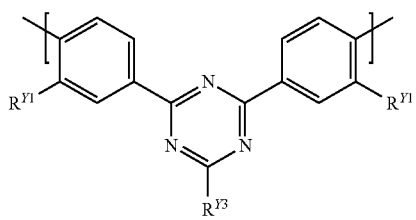
(Y-4′)

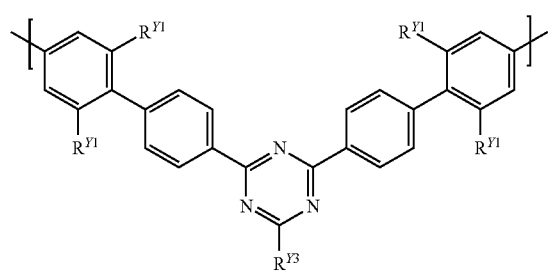
(Y-6′)

[wherein $R^{Y1}$ and $R^{Y3}$ represent the same meaning as described above.]

[Chemical Formula 43]

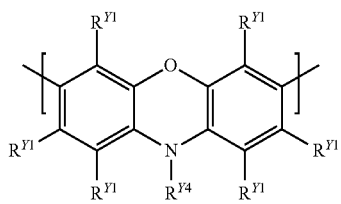
(Y-8)

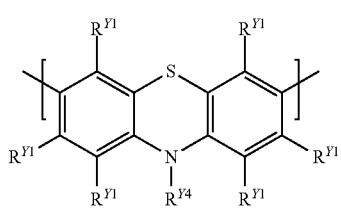
(Y-9)

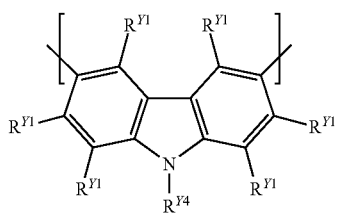
(Y-10)

[wherein $R^{Y1}$ represent the same meaning as described above.

$R^{Y4}$ represents a hydrogen atom, an alkyl group, a cycloalkyl group, an alkoxy group, a cycloalkoxy group, an aryl group or a monovalent heterocyclic group, and the forgoing groups optionally have a substituent].

$R^{Y4}$ is preferably an alkyl group, a cycloalkyl group, an alkoxy group, a cycloalkoxy group, an aryl group or a monovalent heterocyclic group, more preferably an aryl group, and the forgoing groups optionally have a substituent.

The constitutional unit represented by the formula (Y) includes, for example, constitutional units composed of an arylene group represented by the formulae (Y-101)-(Y-121), constitutional units composed of a divalent heterocyclic group represented by the formulae (Y-201)-(Y-206), and constitutional units composed of a divalent group in which at least one arylene group and at least one divalent heterocyclic group are bonded directly represented by the formulae (Y-301)-(Y-304).

[Chemical Formula 44]

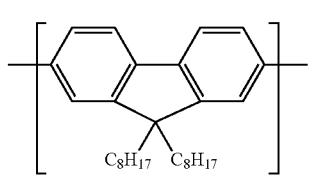
(Y-101)

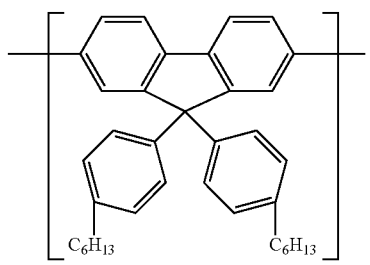
(Y-102)

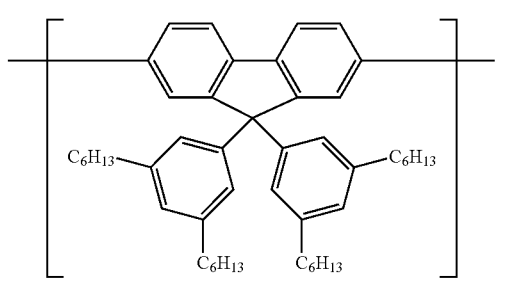
(Y-103)

[Chemical Formula 45]

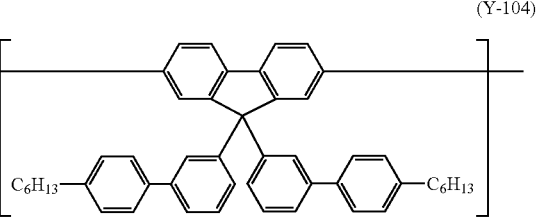
(Y-104)

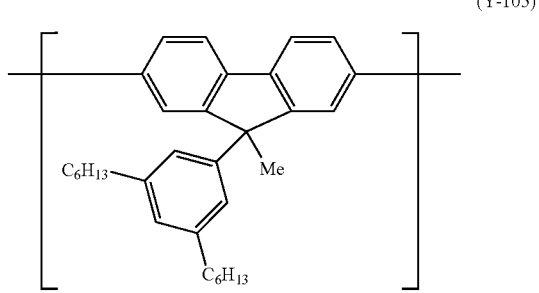
(Y-105)

[Chemical Formula 46]
(Y-106)
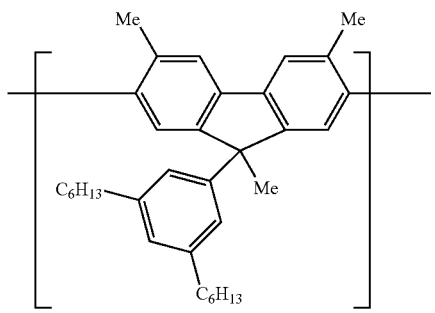
(Y-107)
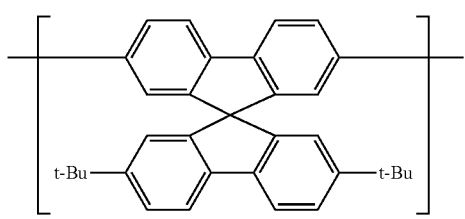
(Y-108)
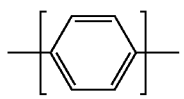
(Y-109)
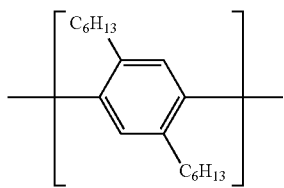
[Chemical Formula 47]
(Y-110)
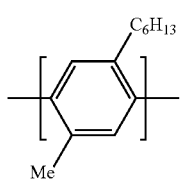
(Y-111)
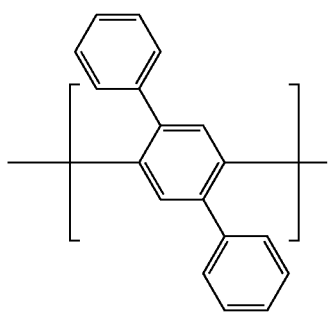
(Y-112)
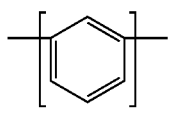
(Y-113)
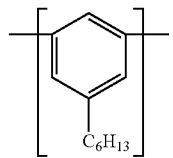
(Y-114)
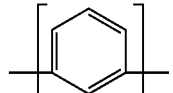
[Chemical Formula 48]
(Y-115)
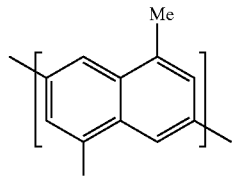
(Y-116)
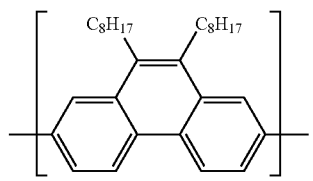
(Y-117)
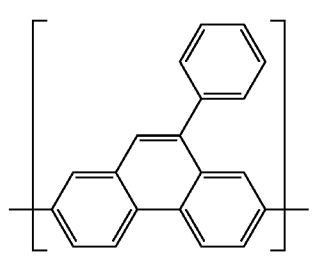
(Y-118)
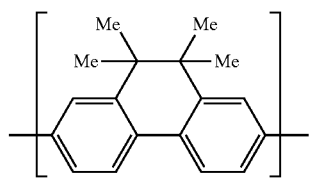
[Chemical Formula 49]
(Y-119)
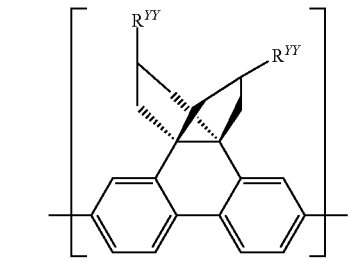

(Y-120)
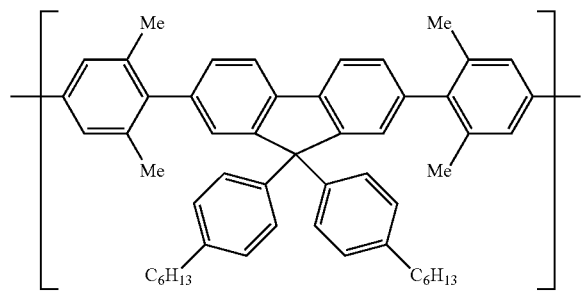
(Y-121)
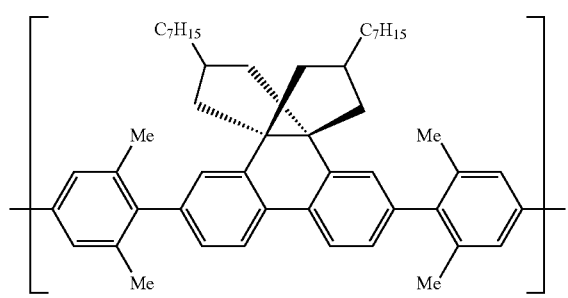
[Chemical Formula 50]
(Y-201)
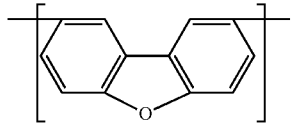
(Y-202)
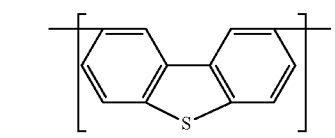
(Y-203)
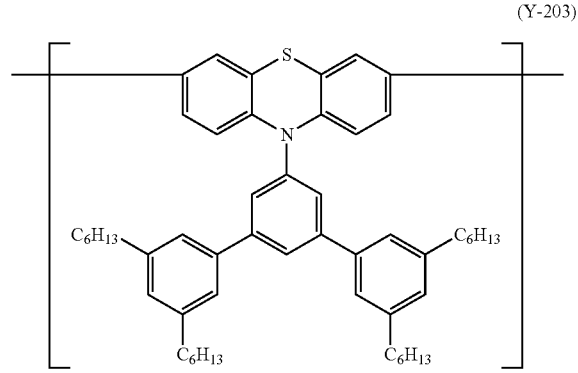
(Y-204)
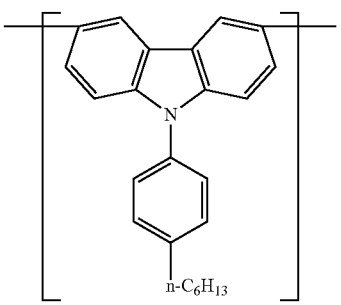
[Chemical Formula 51]
(Y-205)
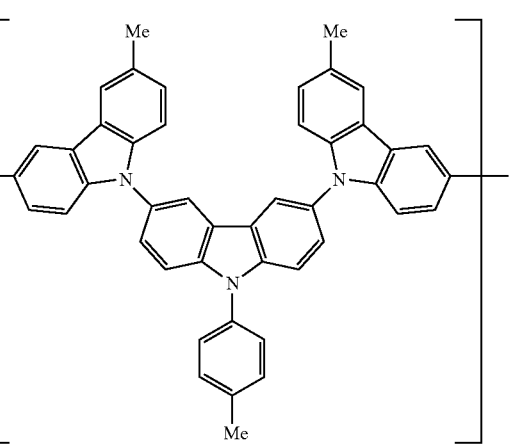
(Y-206)
(Y-301)
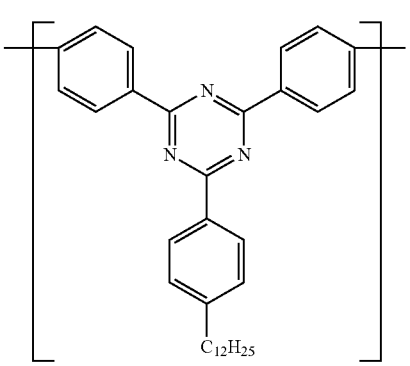

-continued

[Chemical Formula 52]

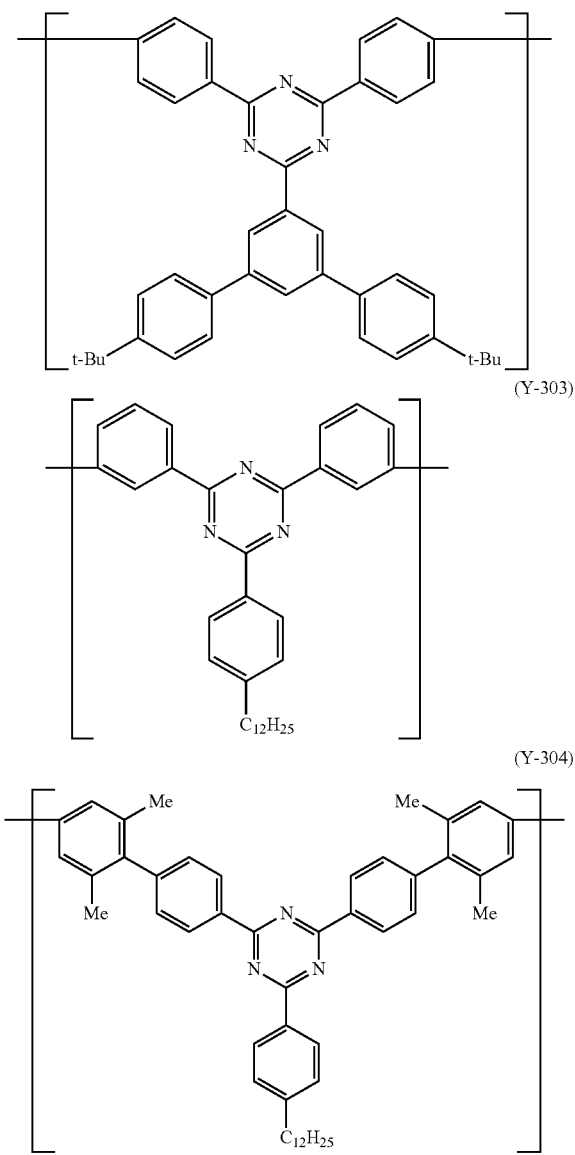

The amount of the constitutional unit represented by the formula (Y) in which $Ar^{y1}$ is an arylene group is preferably 0.5 to 90% by mol, more preferably 30 to 80% by mol with respect to the total amount of constitutional units contained in the polymer compound, since a light emitting device having a film formed by using the composition of the present invention is excellent in luminance life.

The constitutional unit represented by the formula (Y) in which $Ar^{y1}$ is a divalent heterocyclic group or a divalent group in which at least one arylene group and at least one divalent heterocyclic group are bonded directly is preferably 0.5 to 50% by mol, more preferably 3 to 30% by mol with respect to the total amount of constitutional units contained in the polymer compound, since a light emitting device having a film formed by using the composition of the present invention is excellent in light emission efficiency, hole transportability or electron transportability.

The constitutional unit represented by the formula (Y) may be contained singly or two or more kinds of the constitutional units may be contained in the polymer compound.

The polymer compound includes, for example, polymer compounds (P-101) to (P-107) in Table 1.

TABLE 1

| | constitutional unit and molar ratio thereof | | | | |
| --- | --- | --- | --- | --- | --- |
| | formula (Y) | | | formula (X) | |
| polymer compound | formulae (Y-1) to (Y-3) p | formulae (Y-4) to (Y-7) q | formulae (Y-8) to (Y-10) r | formulae (X-1) to (X-7) s | other t |
| (P-101) | 0.1 to 99.9 | 0.1 to 99.9 | 0 | 0 | 0 to 30 |
| (P-102) | 0.1 to 99.9 | 0 | 0.1 to 99.9 | 0 | 0 to 30 |
| (P-103) | 0.1 to 99.9 | 0 | 0 | 0.1 to 99.9 | 0 to 30 |
| (P-104) | 0.1 to 99.8 | 0.1 to 99.8 | 0.1 to 99.8 | 0 | 0 to 30 |
| (P-105) | 0.1 to 99.8 | 0.1 to 99.8 | 0 | 0.1 to 99.8 | 0 to 30 |
| (P-106) | 0.1 to 99.8 | 0 | 0.1 to 99.8 | 0.1 to 99.8 | 0 to 30 |
| (P-107) | 0.1 to 99.7 | 0.1 to 99.7 | 0.1 to 99.7 | 0.1 to 99.7 | 0 to 30 |

[in the table, p, q, r, s and t represent the molar ratio of each constitutional unit. p+q+r+s+t=100 and 100≥p+q+r+s≥70. Other constitutional unit denotes a constitutional unit other than a constitutional unit represented by the formula (Y) and a constitutional unit represented by the formula (X)].

When the polymer compound containing at least one constitutional unit selected from the group consisting of a constitutional unit represented by the formula (X) and a constitutional unit represented by the formula (Y) is used as a light emitting material (that is, when an iridium complex described later is not used together), the polymer compound is preferably a polymer compound containing at least one constitutional unit selected from the group consisting of a constitutional unit represented by the formula (Y-8), a constitutional unit represented by the formula (Y-9) and a constitutional unit represented by the formula (Y-10), more preferably a polymer compound containing at least one constitutional unit selected from the group consisting of a constitutional unit represented by the formula (Y-8) and a constitutional unit represented by the formula (Y-9), further preferably a polymer compound containing a constitutional unit represented by the formula (Y-8).

Further, the polymer compound is preferably a polymer compound containing at least one constitutional unit selected from the group consisting of a constitutional unit represented by the formula (Y-1), a constitutional unit represented by the formula (Y-2), a constitutional unit represented by the formula (Y-3) and a constitutional unit represented by the formula (X), more preferably a polymer compound containing at least one constitutional unit selected from the group consisting of a constitutional unit represented by the formula (Y-1), a constitutional unit represented by the formula (Y-2) and a constitutional unit represented by the formula (X), further preferably a polymer compound containing at least one constitutional unit selected from the group consisting of a constitutional unit represented by the formula (Y-2) and a constitutional unit represented by the formula (X), particularly preferably a polymer compound containing a constitutional unit represented by the formula (Y-2) and a constitutional unit represented by the formula (X), as the constitutional unit other than a constitutional unit represented by the formula (Y-8), a constitutional unit represented by the formula (Y-9) and a constitutional unit represented by the formula (Y-10).

[Production Method of Polymer Compound]

The polymer compound containing at least one constitutional unit selected from the group consisting of a constitutional unit represented by the formula (X) and a constitutional unit represented by the formula (Y) can be produced by using known polymerization methods described in Chemical Review (Chem. Rev.), vol. 109, pp. 897-1091 (2009) and the like, and methods of performing polymerization by a coupling reaction using a transition metal catalyst such as the Suzuki reaction, the Yamamoto reaction, the Buchwald reaction, the Stille reaction, the Negishi reaction, the Kumada reaction and the like are exemplified.

In the above-described polymerization methods, the means of charging monomers includes a means of charging all monomers into the reaction system all at once, a means of charging a part of monomers and reacting them before charging the remaining monomers all at once, continuously or separately, a means of charging monomers continuously or separately, and the like.

The transition metal catalyst includes palladium catalysts, nickel catalysts and the like.

The post treatment of the polymerization reaction is conducted by using known methods, for example, a method of removing water-soluble impurities by liquid-separation, a method of adding the reaction liquid after the polymerization reaction to a lower alcohol such as methanol and the like, filtrating the deposited precipitate, then, drying it, and the like, singly or in combination. When the purity of the polymer compound is low, it can be purified by usual methods such as, for example, recrystallization, reprecipitation, continuous extraction with a Soxhlet extractor, column chromatography and the like.

[Iridium Complex]

The organic EL material is preferably an iridium complex, since a light emitting device having a film formed by using the composition of the present invention is excellent in light emission efficiency.

In the composition of the present invention, the iridium complex may be contained singly or two or more kinds of the iridium complexes may be contained.

The iridium complex is preferably an iridium complex represented by the formula (Ir-1), an iridium complex represented by the formula (Ir-2), an iridium complex represented by the formula (Ir-3), an iridium complex represented by the formula (Ir-4) or an iridium complex represented by the formula (Ir-5), more preferably an iridium complex represented by the formula (Ir-1), an iridium complex represented by the formula (Ir-2) or an iridium complex represented by the formula (Ir-3), since a light emitting device having a film formed by using the composition of the present invention is more excellent in light emission efficiency.

[Chemical Formula 53]

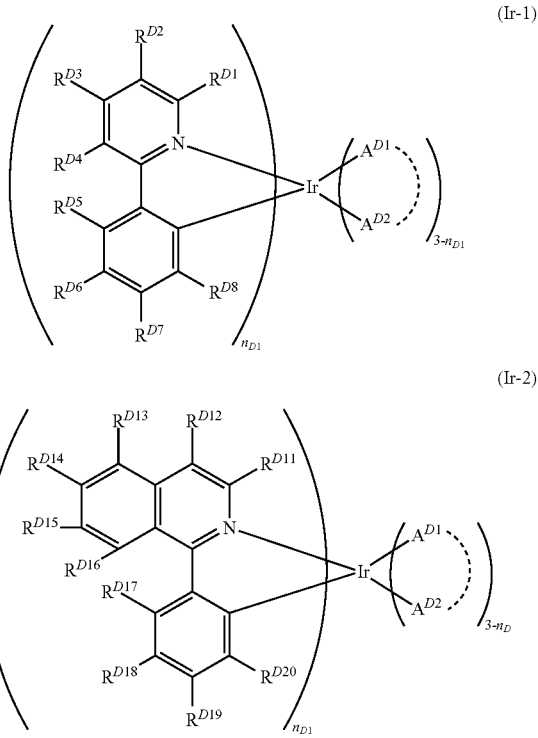

[Chemical Formula 54]

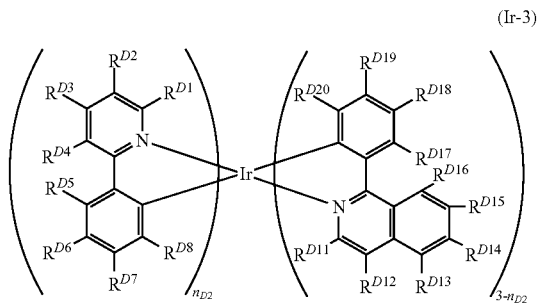

[Chemical Formula 55]

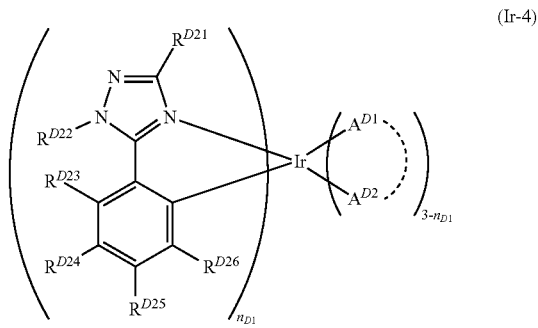

-continued

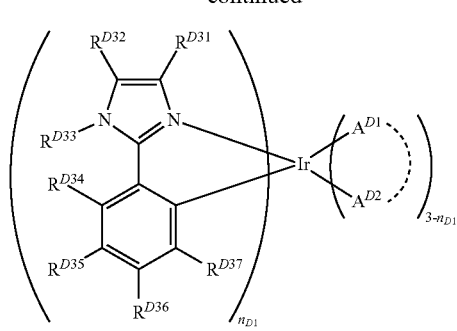
(Ir-5)

[wherein $n_{D1}$ represents 1, 2 or 3. $n_{D2}$ represents 1 or 2.

$R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$ and $R^{D37}$ each independently represent a hydrogen atom, an alkyl group, a cycloalkyl group, an alkoxy group, a cycloalkoxy group, an aryl group, an aryloxy group, a monovalent heterocyclic group or a halogen atom, and the forgoing groups optionally have a substituent. When a plurality of $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$ and $R^{D37}$ are present, they may be the same or different at each occurrence.

-$A^{D1}$---$A^{D2}$- represents an anionic bidentate ligand. $A^{D1}$ and $A^{D2}$ each independently represent a carbon atom, an oxygen atom or a nitrogen atom bonding to an iridium atom, and these atoms may be ring constituent atoms. When a plurality of -$A^{D1}$---$A^{D2}$- are present, they may be the same or different].

In the iridium complex represented by the formula (Ir-1), at least one of $R^{D1}$ to $R^{D8}$ is preferably a group represented by the formula (D-A).

In the iridium complex represented by the formula (Ir-2), at least one of $R^{D11}$ to $R^{D20}$ is preferably a group represented by the formula (D-A).

In the iridium complex represented by the formula (Ir-3), at least one of $R^{D1}$ to $R^{D8}$ and $R^{D11}$ to $R^{D2}$ is preferably a group represented by the formula (D-A).

In the iridium complex represented by the formula (Ir-4), at least one of $R^{21}$ to $R^{D26}$ is preferably a group represented by the formula (D-A).

In the iridium complex represented by the formula (Ir-5), at least one of $R^{D31}$ to $R^{D37}$ is preferably a group represented by the formula (D-A).

[Chemical Formula 56]

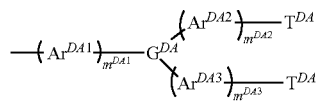
(D-A)

[wherein $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, and the forgoing groups optionally have a substituent.

$Ar^{DA1}$, $Ar^{DA2}$ and $Ar^{DA3}$ each independently represent an arylene group or a divalent heterocyclic group, and the forgoing groups optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and the forgoing groups optionally have a substituent. A plurality of $T^{DA}$ may be the same or different.]

$m^{DA1}$ $m^{DA2}$ and $m^{DA3}$ are usually an integer of 10 or less, preferably an integer of 5 or less, more preferably 0 or 1. It is preferable that $m^{DA1}$ $m^{DA2}$ and $m^{DA3}$ are the same integer.

$G^{DA}$ represents preferably groups represented by the formulae (GDA-11) to (GDA-15), and the forgoing groups optionally have a substituent.

[Chemical Formula 57]

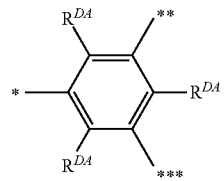
(GDA-11)

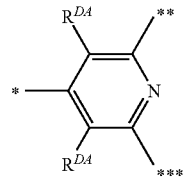
(GDA-12)

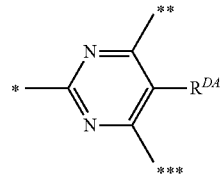
(GDA-13)

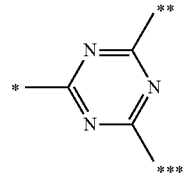
(GDA-14)

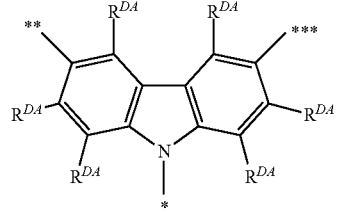
(GDA-15)

[wherein

*,  and * represent bonds to $Ar^{DA1}$, $Ar^{DA2}$ and $Ar^{DA3}$, respectively.

$R^{DA}$ represents a hydrogen atom, an alkyl group, a cycloalkyl group, an alkoxy group, a cycloalkoxy group, an aryl group or a monovalent heterocyclic group, and the foregoing groups optionally further have a substituent. When a plurality of $R^{DA}$ are present, they may be the same or different].

$R^{DA}$ is preferably a hydrogen atom, an alkyl group, a cycloalkyl group, an alkoxy group or a cycloalkoxy group, more preferably a hydrogen atom, an alkyl group or a cycloalkyl group, and the forgoing groups optionally have a substituent.

$Ar^{DA1}$, $Ar^{DA2}$ and $Ar^{DA3}$ are preferably groups represented by the formulae (ArDA-1) to (ArDA-3).

[Chemical Formula 58]

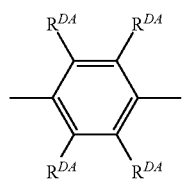
(ArDA-1)

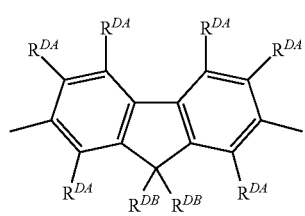
(ArDA-2)

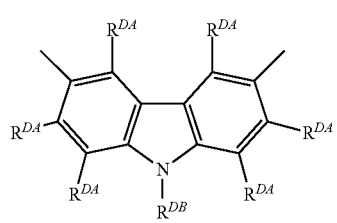
(ArDA-3)

[wherein $R^{DA}$ represents the same meaning as described above.

$R^{DB}$ represents a hydrogen atom, alkyl group, cycloalkyl group, aryl group or monovalent heterocyclic group, and the forgoing groups optionally have a substituent. When a plurality of $R^{DB}$ are present, they may be the same or different].

$T^{DA}$ is preferably a group represented by the formulae (TDA-1) to (TDA-3).

[Chemical Formula 59]

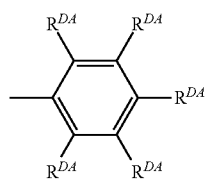
(TDA-1)

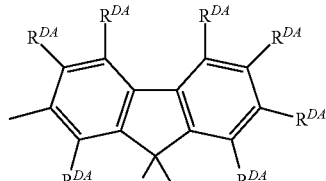
(TDA-2)

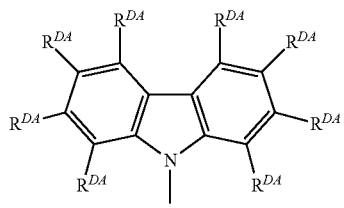
(TDA-3)

[wherein $R^{DA}$ and $R^{DB}$ represent the same meaning as described above.]

The group represented by the formula (D-A) is preferably a group represented by the formulae (D-A1) to (D-A3).

[Chemical Formula 60]

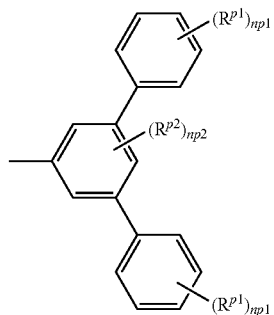
(D-A1)

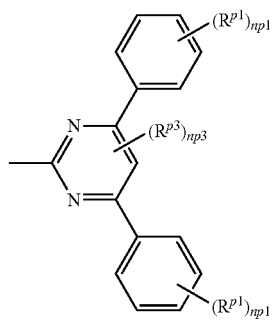
(D-A2)

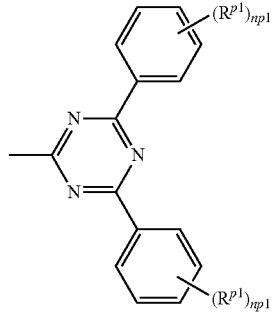
(D-A3)

[wherein np1 represents an integer of 0 to 5, np2 represents an integer of 0 to 3, and np3 represents 0 or 1. A plurality of np1 may be the same or different.

$R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence].

np1 is preferably 0 or 1, more preferably 1. np2 is preferably 0 or 1, more preferably 0. np3 is preferably 0.

$R^{p1}$, $R^{p2}$ and $R^{p3}$ represent preferably an alkyl group or a cycloalkyl group.

The anionic bidentate ligand represented by -$A^{D1}$---$A^{D2}$- includes, for example, ligands represented by the following formulae.

[Chemical Formula 61]

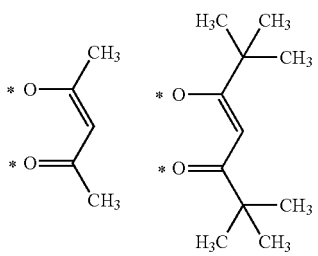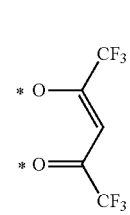

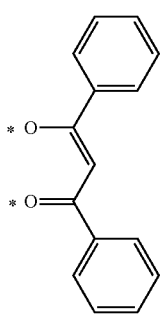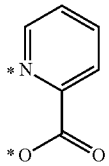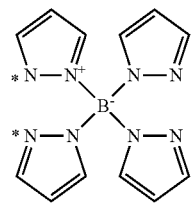

[wherein * represents a site binding to an iridium atom.]

The iridium complex represented by the formula (Ir-1) is preferably an iridium complex represented by the formula (Ir-11) to the formula (Ir-13). The iridium complex represented by the formula (Ir-2) is preferably an iridium complex represented by the formula (Ir-21). The iridium complex represented by the formula (Ir-3) is preferably an iridium complex represented by the formula (Ir-31) to the formula (Ir-33). The iridium complex represented by the formula (Ir-4) is preferably an iridium complex represented by the formula (Ir-41) to the formula (Ir-43). The iridium complex represented by the formula (Ir-5) is preferably an iridium complex represented by the formula (Ir-51) to the formula (Ir-53).

[Chemical Formula 62]

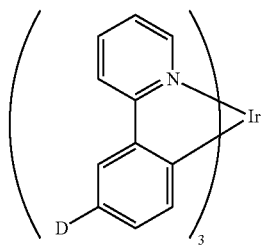
(Ir-11)

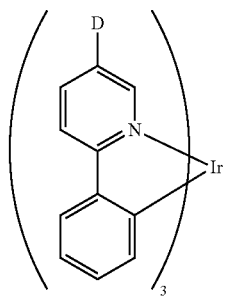
(Ir-12)

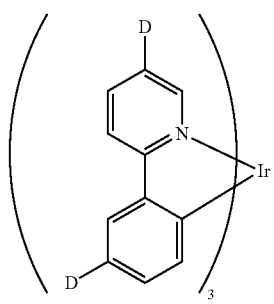
(Ir-13)

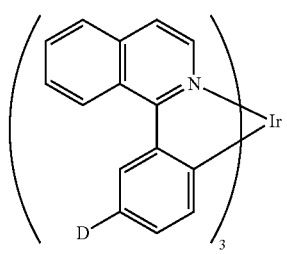
(Ir-21)

[Chemical Formula 63]

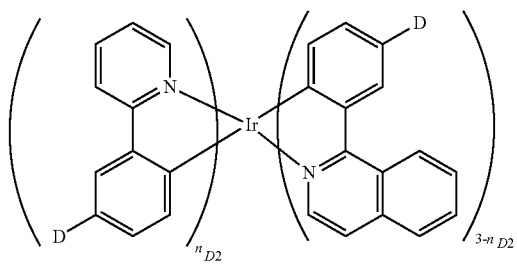
(Ir-31)

(Ir-32)

[Chemical Formula 64]

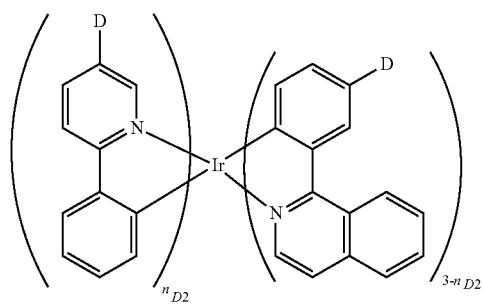

(Ir-33)

[Chemical Formula 65]

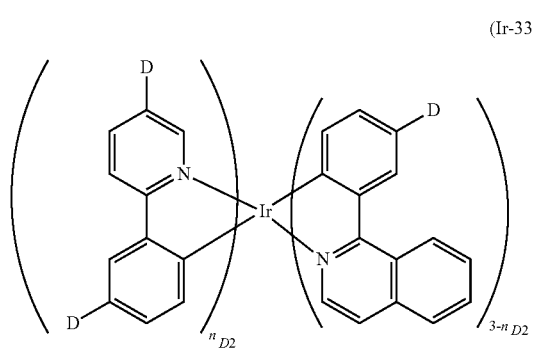

(Ir-41)

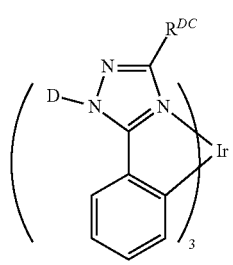

(Ir-42)

(Ir-43)

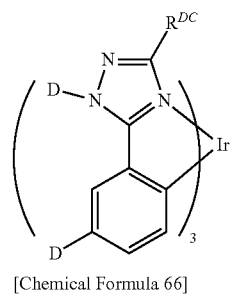

[Chemical Formula 66]

(Ir-51)

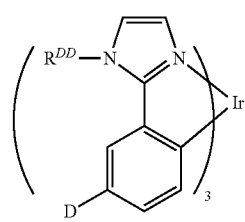

(Ir-52)

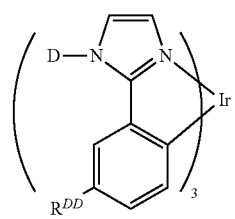

(Ir-53)

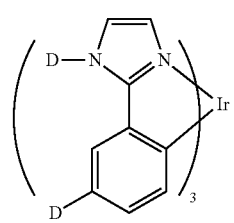

[wherein $n_{D2}$ represents 1 or 2.

D represents a group represented by the formula (D-A). A plurality of D may be the same or different.

$R^{DC}$ represents a hydrogen atom, an alkyl group, a cycloalkyl group, an aryl group or a monovalent heterocyclic group, and the forgoing groups optionally have a substituent. A plurality of $R^{DC}$ may be the same or different.

$R^{DD}$ represents an alkyl group, a cycloalkyl group, an aryl group or a monovalent heterocyclic group, and the forgoing groups optionally have a substituent. A plurality of $R^{DD}$ may be the same or different.]

The iridium complex includes, for example, iridium complexes represented by the following formulae.

[Chemical Formula 67]
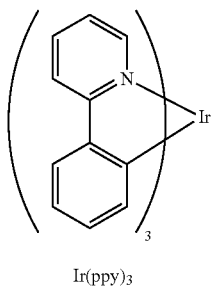
Ir(ppy)₃
COM-1
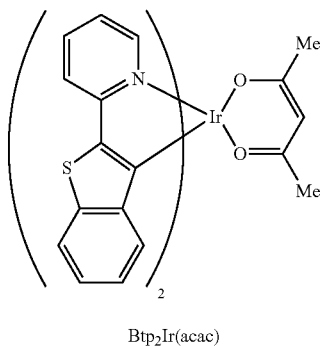
Btp₂Ir(acac)
COM-2
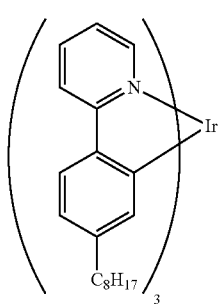
COM-3
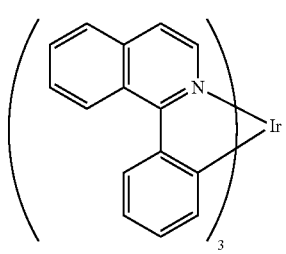
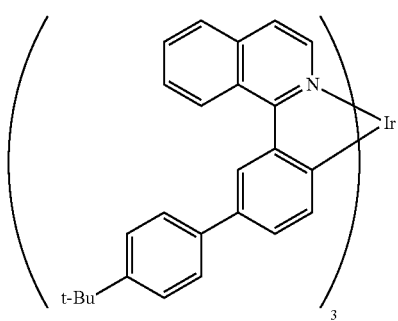
[Chemical Formula 68]
COM-4
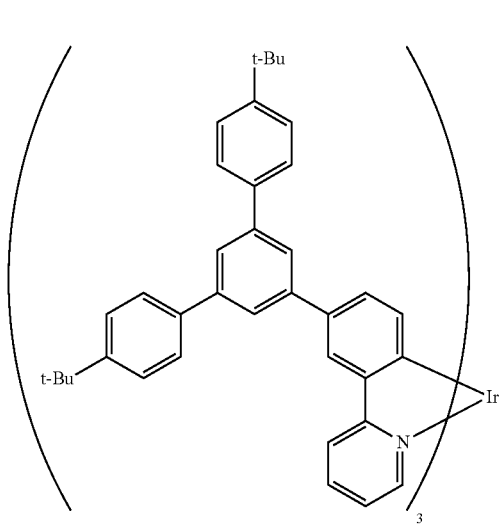
COM-5
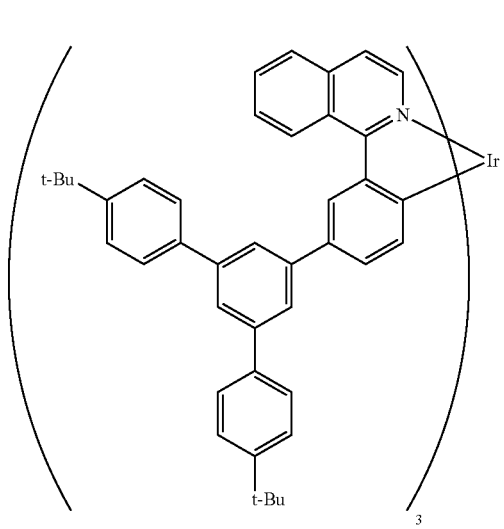

-continued
COM-6
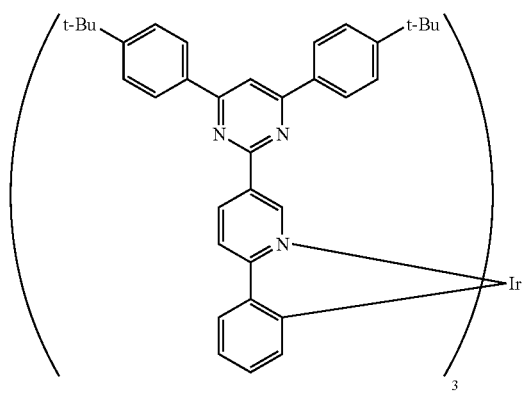
[Chemical Formula 69]
COM-7
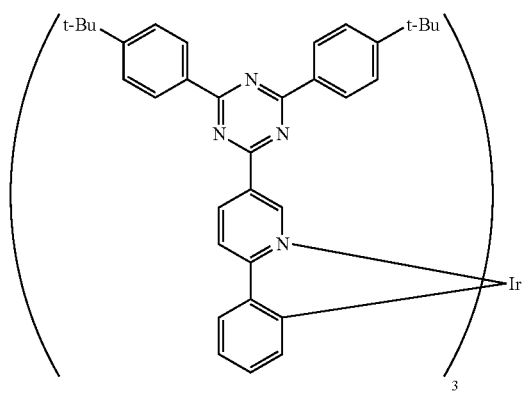
COM-8
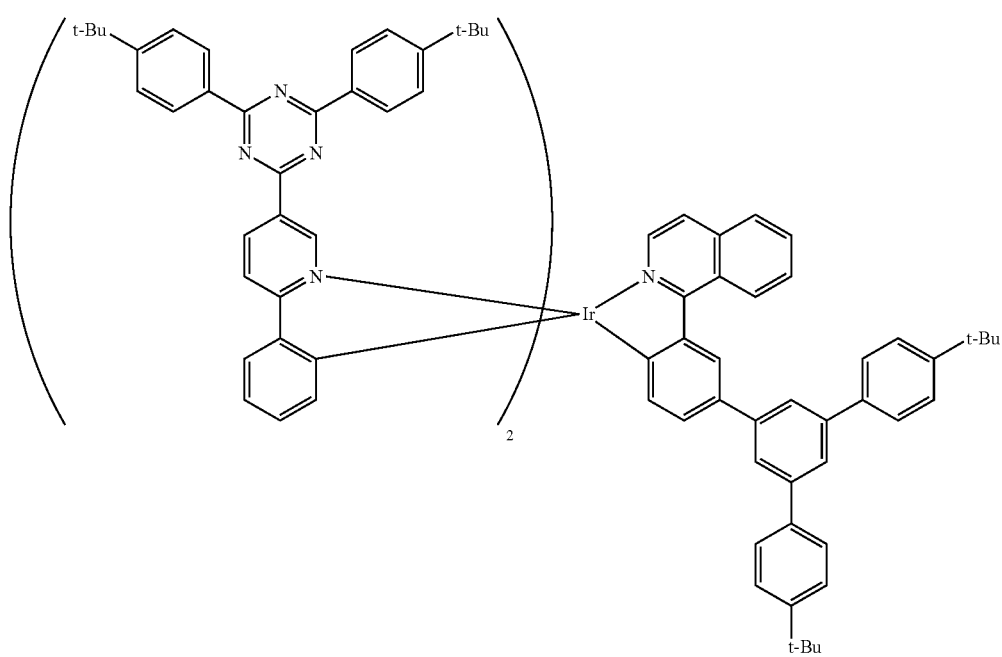

-continued
[Chemical Formula 70]
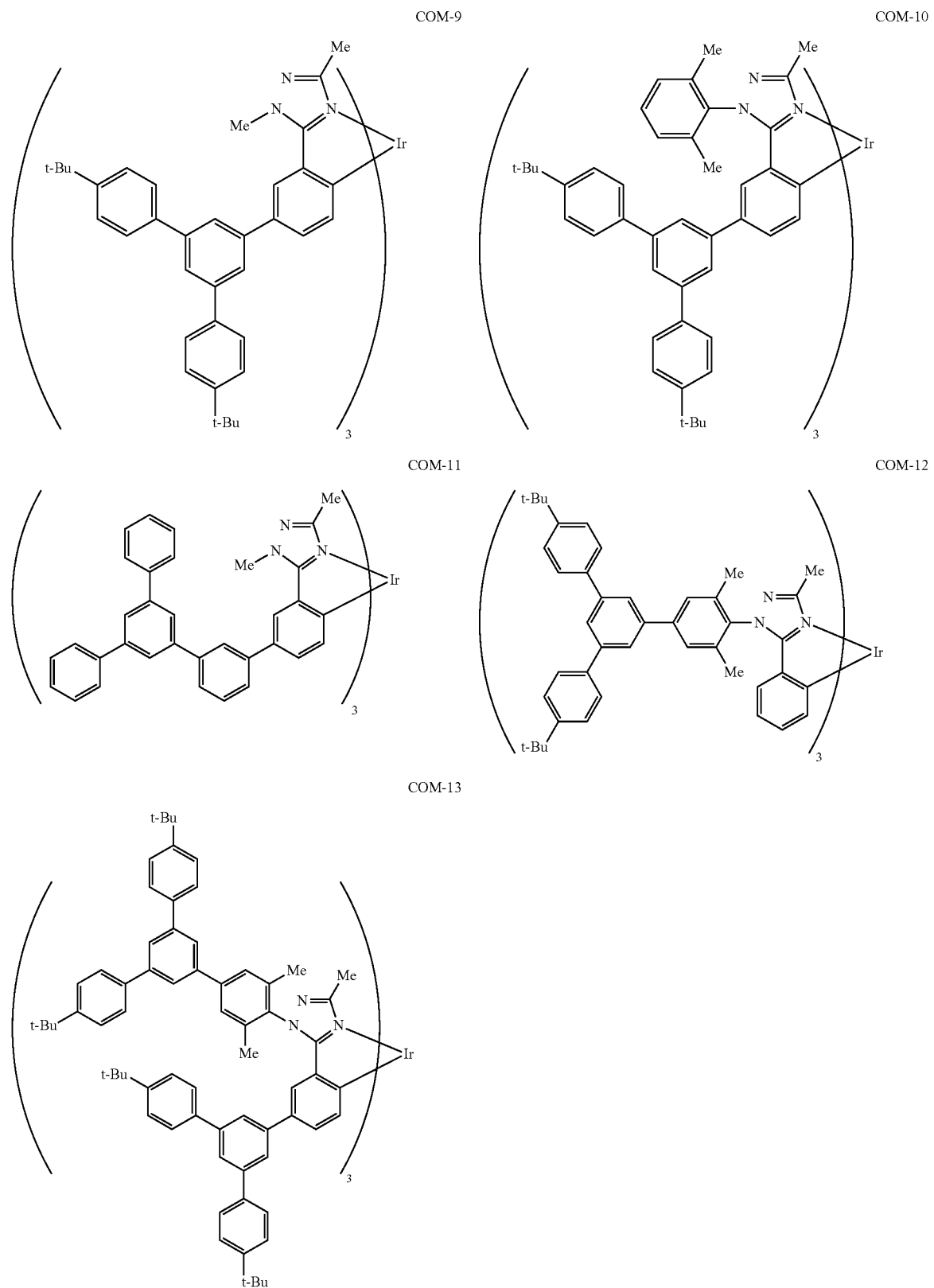

-continued
[Chemical Formula 71]
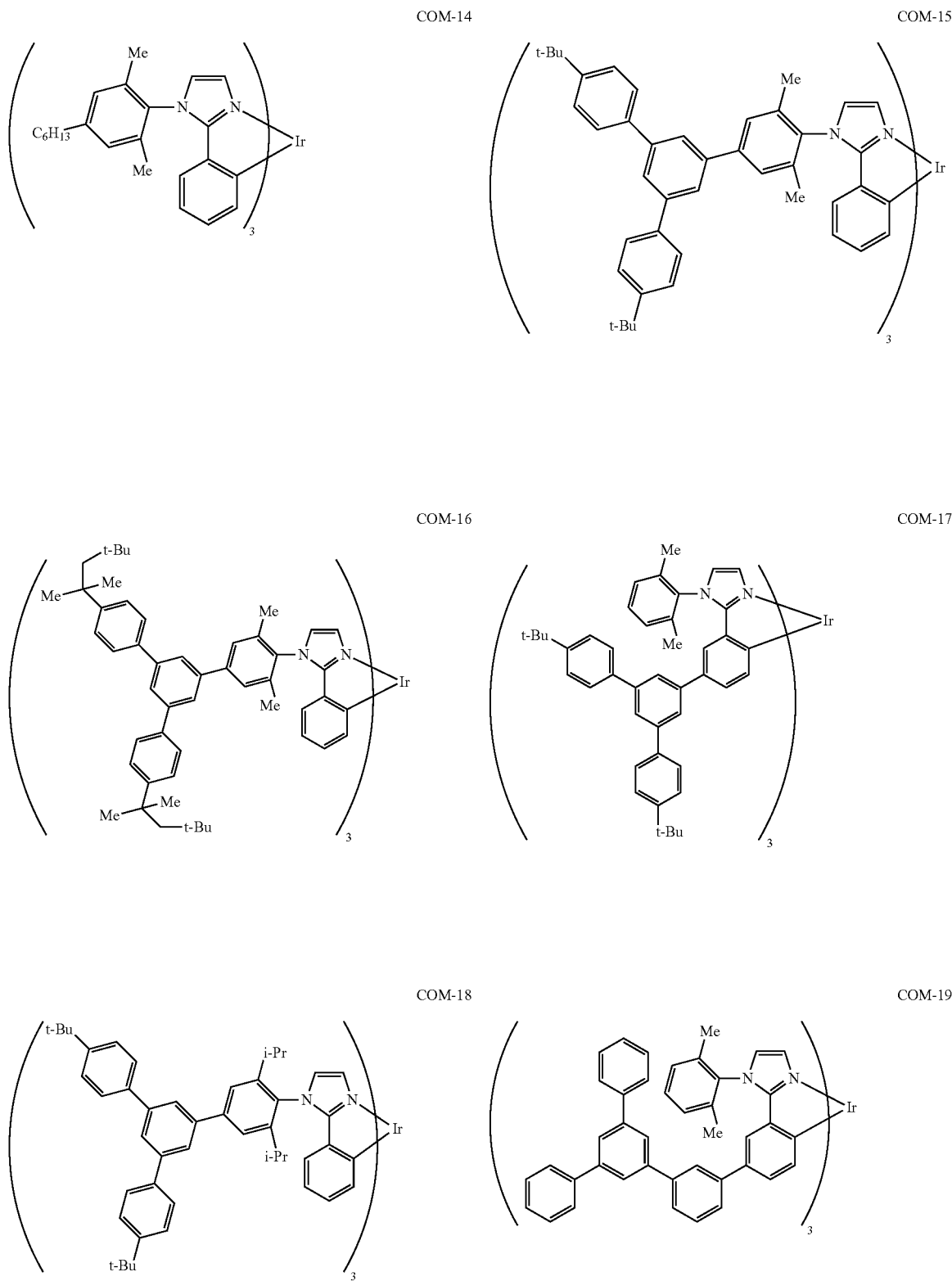

-continued
COM-20

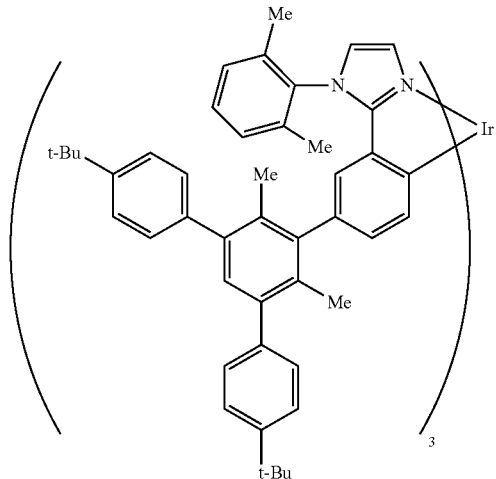

The iridium complex can be synthesized according to methods described, for example, in Japanese Patent Application National Publication No. 2004-530254, Japanese Patent Application National Publication No. 2008-179617, Japanese Patent Application National Publication No. 2011-105701, Japanese Patent Application National Publication No. 2007-504272, Japanese Patent Application National Publication No. 2013-147449 and Japanese Patent Application National Publication No. 2013-147450.

[Polymer Compound Containing Constitutional Unit Having Structure of Iridium Complex]

The iridium complex may also be a polymer compound containing a constitutional unit having a structure of an iridium complex (that is, a constitutional unit having a group obtained by removing at least one hydrogen atom bonding directly to a carbon atom or a hetero atom constituting the iridium complex. Hereinafter, referred to also as "iridium complex constitutional unit".).

The iridium complex constitutional unit is a constitutional unit having a structure of an iridium complex represented by the formula (Ir-1), the formula (Ir-2), the formula (Ir-3), the formula (Ir-4) or the formula (Ir-5). The constitutional unit having a structure of an iridium complex represented by the formula (Ir-1), the formula (Ir-2), the formula (Ir-3), the formula (Ir-4) or the formula (Ir-5) is preferably a constitutional unit having a group obtained by removing from an iridium complex represented by the formula (Ir-1), the formula (Ir-2), the formula (Ir-3), the formula (Ir-4) or the formula (Ir-5) one or more and three or less hydrogen atoms bonding directly to a carbon atom or a hetero atom constituting the complex, more preferably a constitutional unit having a group obtained by removing from an iridium complex represented by the formula (Ir-1), the formula (Ir-2), the formula (Ir-3), the formula (Ir-4) or the formula (Ir-5) two hydrogen atoms bonding directly to a carbon atom or a hetero atom constituting the complex.

Additionally, the polymer compound containing the iridium complex constitutional unit is preferably a polymer compound containing at least one constitutional unit selected from the group consisting of a constitutional unit represented by the formula (X) and a constitutional unit represented by the formula (Y) described above.

Of them, the polymer compound containing the iridium complex constitutional unit is preferably a polymer compound containing at least one constitutional unit selected from the group consisting of a constitutional unit represented by the formula (Y-4), a constitutional unit represented by the formula (Y-5), a constitutional unit represented by the formula (Y-6) and a constitutional unit represented by the formula (Y-7), more preferably a polymer compound containing at least one constitutional unit selected from the group consisting of a constitutional unit represented by the formula (Y-4) and a constitutional unit represented by the formula (Y-6), further preferably a polymer compound containing a constitutional unit represented by the formula (Y-4).

Further, the polymer compound containing the iridium complex constitutional unit is preferably a polymer compound containing at least one constitutional unit selected from the group consisting of a constitutional unit represented by the formula (Y-1), a constitutional unit represented by the formula (Y-2), a constitutional unit represented by the formula (Y-3) and a constitutional unit represented by the formula (X), more preferably a polymer compound containing at least one constitutional unit selected from the group consisting of a constitutional unit represented by the formula (Y-1), a constitutional unit represented by the formula (Y-2) and a constitutional unit represented by the formula (X), as the constitutional unit other than a constitutional unit represented by the formula (Y-4), a constitutional unit represented by the formula (Y-5), a constitutional unit represented by the formula (Y-6) and a constitutional unit represented by the formula (Y-7).

The iridium complex constitutional unit may be contained singly or two or more kinds of the iridium complex constitutional units may be contained in the polymer compound.

[Host Material]

When the iridium complex is used together with a host material having at least one function selected from hole transportability, hole injectability, electron transportability and electron injectability, a light emitting device having a film formed by using the composition of the present invention is excellent in light emission efficiency. That is, if the composition of the present invention contains an iridium complex as the organic EL material, it is preferable that the composition of the present invention contains an iridium complex and a host material as the organic EL material.

If the composition of the present invention contains a host material, the host material may be contained singly or two or more kinds of the host materials may be contained.

If the composition of the present invention contains an iridium complex and a host material as the organic EL material, the content of the iridium complex is usually 0.05 to 80 parts by weight, preferably 0.1 to 50 parts by weight, more preferably 0.5 to 40 parts by weight, when the total content of the iridium complex and the host material is 100 parts by weight.

It is preferable that the lowest excited triplet state ($T_1$) of the host material is at energy level equivalent to or higher than $T_1$ of the iridium complex, since a light emitting device having a film formed by using the composition of the present invention is excellent in light emission efficiency.

The host material is classified into a low molecular weight compound (hereinafter, referred to also as "low molecular weight host") and a polymer compound (hereinafter, referred to also as "polymer host"), and may be any of a low molecular weight host and a polymer host, and a polymer host is preferable.

The low molecular weight host includes, for example, compounds having a carbazole structure, compounds having a triarylamine structure, compounds having a phenanthroline structure, compounds having a triaryltriazine structure, compounds having an azole structure, compounds having a benzothiophene structure, compounds having a benzofuran structure, compounds having a fluorene structure, compounds having a spirofluorene structure, and the like.

Specific examples of the low molecular weight host include compounds represented by the following formulae.

[Chemical Formula 72]

[Chemical Formula 73]

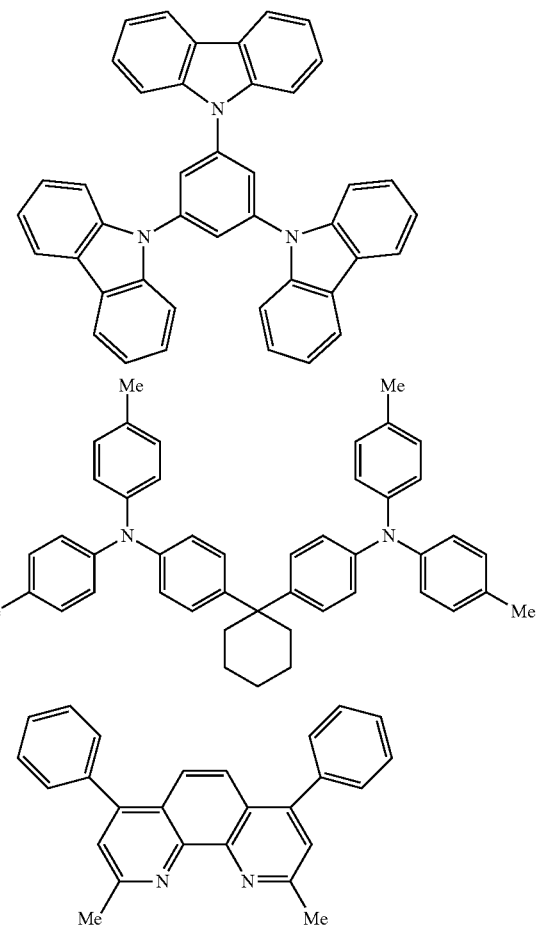

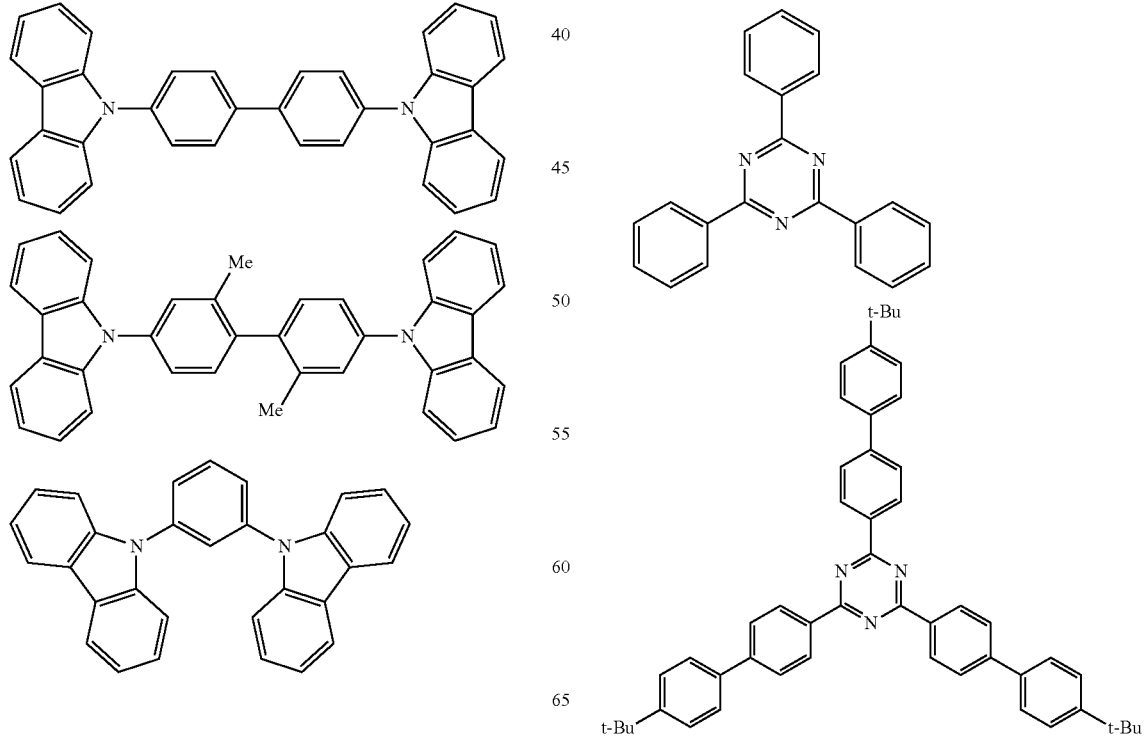

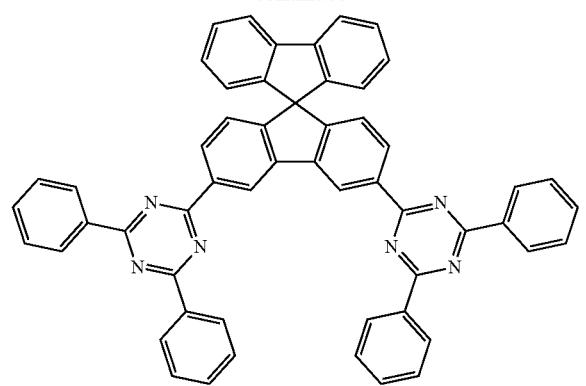
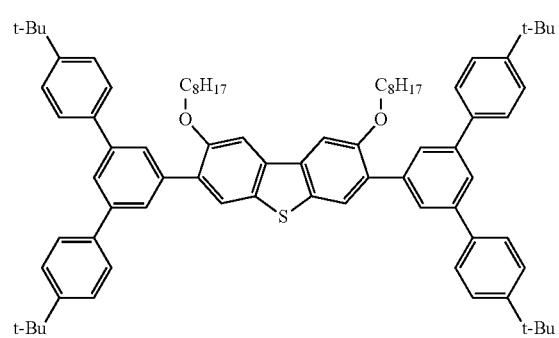
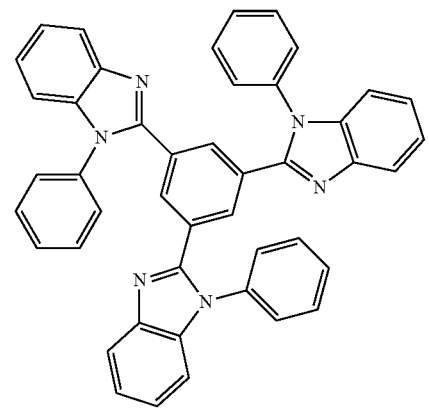
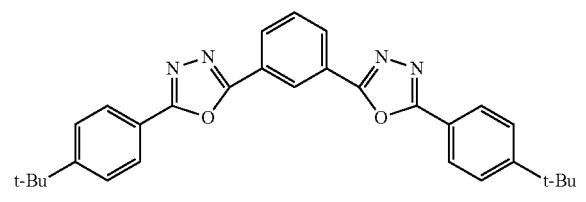
[Chemical Formula 74]
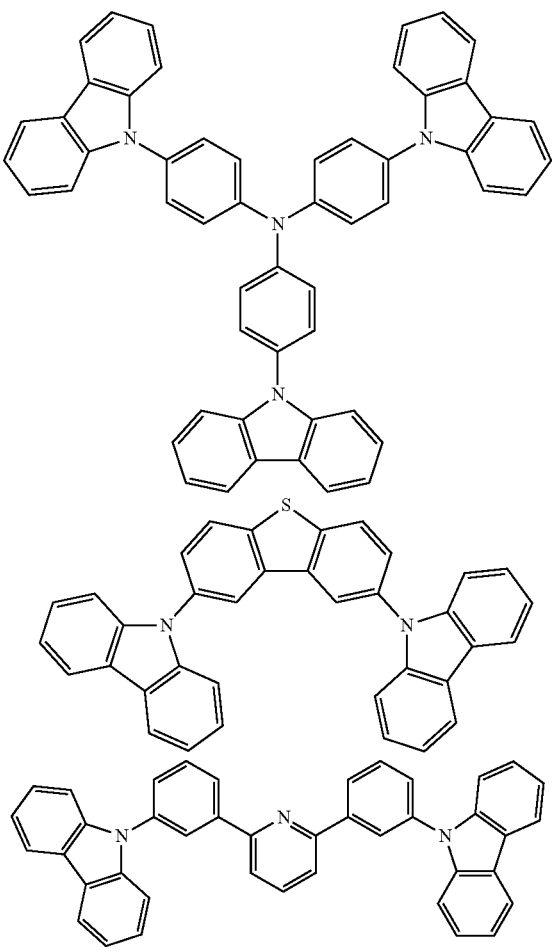
[Chemical Formula 75]
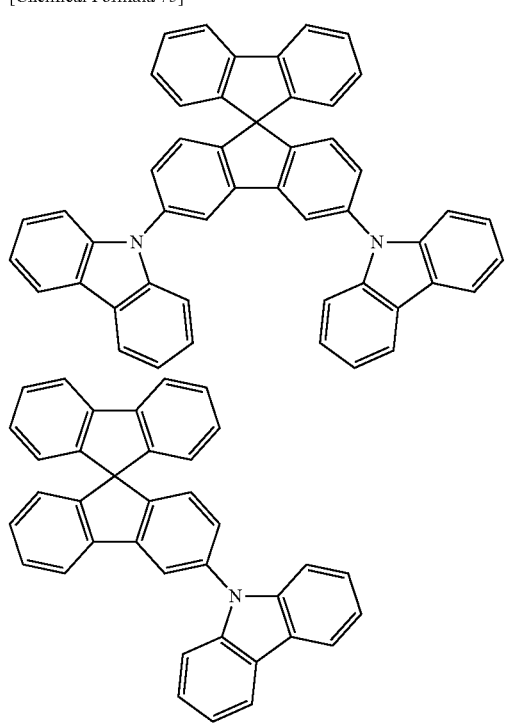

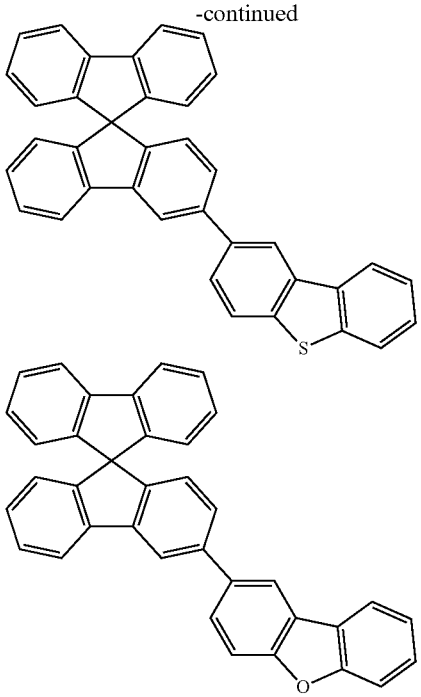

The polymer host is preferably a polymer compound containing at least one constitutional unit selected from the group consisting of a constitutional unit represented by the formula (X) and a constitutional unit represented by the formula (Y) described above.

Of them, the polymer host is preferably a polymer compound containing at least one constitutional unit selected from the group consisting of a constitutional unit represented by the formula (Y-4), a constitutional unit represented by the formula (Y-5), a constitutional unit represented by the formula (Y-6) and a constitutional unit represented by the formula (Y-7), more preferably a polymer compound containing at least one constitutional unit selected from the group consisting of a constitutional unit represented by the formula (Y-4) and a constitutional unit represented by the formula (Y-6), further preferably a polymer compound containing a constitutional unit represented by the formula (Y-4).

Further, the polymer host is preferably a polymer compound containing at least one constitutional unit selected from the group consisting of a constitutional unit represented by the formula (Y-1), a constitutional unit represented by the formula (Y-2), a constitutional unit represented by the formula (Y-3) and a constitutional unit represented by the formula (X), more preferably a polymer compound containing at least one constitutional unit selected from the group consisting of a constitutional unit represented by the formula (Y-1), a constitutional unit represented by the formula (Y-2) and a constitutional unit represented by the formula (X), as the constitutional unit other than a constitutional unit represented by the formula (Y-4), a constitutional unit represented by the formula (Y-5), a constitutional unit represented by the formula (Y-6) and a constitutional unit represented by the formula (Y-7).

[Other Organic EL Material]

The organic EL material contained in the composition of the present invention may also be a hole transporting material, a hole injection material, an electron transporting material, an electron injection material and a light emitting material described later.

[Hole Transporting Material]

The hole transporting material is classified into low molecular weight compounds and polymer compounds, and preferable are polymer compounds, more preferable are polymer compounds having a crosslink group.

The polymer compound includes, for example, polyvinylcarbazole and derivatives thereof; and polyarylenes having an aromatic amine structure in the side chain or the main chain and derivatives thereof. The polymer compound may also be a compound in which an electron accepting portion is bonded. The electron accepting portion includes, for example, fullerene, tetrafluorotetracyanoquinodimethane, tetracyanoethylene, trinitrofluorenone and the like, and preferable is fullerene.

The hole transporting material may be contained singly or two or more kinds of the hole transporting materials may be contained in the composition of the present invention.

[Electron Transporting Material]

The electron transporting material is classified into low molecular weight compounds and polymer compounds. The electron transporting material optionally has a crosslink group.

The low molecular weight compound includes, for example, metal complexes having 8-hydroxyquinoline as the ligand, oxadiazole, anthraquinodimethane, benzoquinone, naphthoquinone, anthraquinone, tetracyanoanthraquinodimethane, fluorenone, diphenyldicyanoethylene and diphenoquinone, and derivatives thereof.

The polymer compound includes, for example, polyphenylene, polyfluorene, and derivatives thereof. The polymer compound may be doped with a metal.

The electron transporting material may be contained singly or two or more kinds of the electron transporting materials may be contained in the composition of the present invention.

[Hole Injection Material and Electron Injection Material]

The hole injection material and the electron injection material are each classified into low molecular weight compounds and polymer compounds. The hole injection material and the electron injection material optionally have a crosslink group.

The low molecular weight compound includes, for example, metallic phthalocyanines such as copper phthalocyanine and the like; carbon; oxides of metals such as molybdenum, tungsten and the like; metal fluorides such as lithium fluoride, sodium fluoride, cesium fluoride, potassium fluoride and the like.

The polymer compound includes, for example, electrically conductive polymers such as polyaniline, polythiophene, polypyrrole, polyphenylenevinylene, polythienylenevinylene, polyquinoline and polyquinoxaline, and derivatives thereof; polymers containing an aromatic amine structure in the main chain or the side chain, and the like.

The hole injection material and the electron injection material may be contained each singly or two or more kinds of the hole injection materials and two or more kinds of the electron injection materials may be contained, respectively, in the composition of the present invention.

When the hole injection material or the electron injection material contains an electrically conductive polymer, the electric conductivity of the electrically conductive polymer is preferably $1 \times 10^{-5}$ S/cm to $1 \times 10^{3}$ S/cm. The electrically conductive polymer can be doped with a suitable amount of ions for adjusting the electric conductivity of the electrically conductive polymer in such a range.

The ion to be doped is an anion in the case of the hole injection material, and is a cation in the case of the electron injection material. The anion includes, for example, a polystyrenesulfonate ion, an alkylbenzenesulfonate ion and a camphor sulfonate ion. The cation includes, for example, a lithium ion, a sodium ion, a potassium ion and a tetrabutyl ammonium ion.

The ion to be doped may be used singly or two or more kinds of the ions may be used in combination.

[Light Emitting Material]

The light emitting material includes, for example, naphthalene and derivatives thereof, anthracene and derivatives thereof, and perylene and derivatives thereof.

In the composition of the present invention, the light emitting material may be contained singly or two or more kinds of the light emitting materials may be contained.

[Antioxidant]

The composition of the present invention may contain an antioxidant soluble in a solvent (A), an aromatic hydrocarbon solvent (B) or aromatic ether compound (C) and which does not disturb light emission and charge transportation. The antioxidant includes, for example, phenol type antioxidants and phosphorus-based antioxidants.

In the composition of the present invention, the antioxidant may be contained singly or two or more kinds of the antioxidants may be contained.

<Composition Ratio>

The composition of the present invention is a composition containing an organic EL material, a solvent (A), an aromatic hydrocarbon solvent (B) and an aromatic ether solvent (C).

In the composition of the present invention, the content of an organic EL material is usually 0.1 to 10.0 parts by weight when the total content of an organic EL material, a solvent (A), an aromatic hydrocarbon solvent (B) and an aromatic ether solvent (C) is 100 parts by weight, and it is preferably 0.2 to 7.0 parts by weight, more preferably 0.3 to 5.0 parts by weight, since dischargeability in an inkjet printing method is excellent.

When the composition of the present invention contains the solvent (D), the content of an organic EL material is usually 0.05 to 10.0 parts by weight when the total content of an organic EL material, a solvent (A), an aromatic hydrocarbon solvent (B), an aromatic ether solvent (C) and the solvent (D) is 100 parts by weight, and it is preferably 0.1 to 7.0 parts by weight, more preferably 0.2 to 5.0 parts by weight, since dischargeability in an inkjet printing method is excellent.

<Film>

The film is a film formed by using the composition of the present invention. In the film, an organic EL material is contained.

In the film, an organic EL material may be contained as it is, or an organic EL material may be contained in intramolecularly crosslinked condition or intermolecularly cross linked condition, or intramolecularly and intermolecularly crosslinked condition (crosslinked body). The film containing a crosslinked body of an organic EL material is a film obtained by crosslinking a film containing an organic EL material by an external stimulus such as heating, light irradiation and the like. The film containing a crosslinked body of an organic EL material can be suitably used for lamination of a light emitting device, since it is substantially insolubilized in a solvent.

The temperature of heating for cross-linking the film is usually 25 to 300° C., preferably 50 to 250° C., more preferably 150 to 200° C.

The light used in light irradiation for cross-linking the film is, for example, ultraviolet light, near ultraviolet light, visible light and infrared light.

The film is suitable as a light emitting layer, a hole transporting layer or a hole injection layer in a light emitting device.

The film can be fabricated, for example, by a spin coat method, a casting method, a micro gravure method, a gravure method, a bar coat method, a roll coat method, a wire bar coat method, a dip coat method, a spray coat method, a screen printing method, a flexo printing method, an offset printing method, an inkjet printing method, a capillary coat method or a nozzle coat method, using the composition of the present invention, and a film fabricated by an inkjet printing method as a discharge type application method, and the like, is excellent in its flatness.

The thickness of the film is usually 1 nm to 10 μm.

<Light Emitting Device>

The light emitting device of the present invention is a light emitting device having a film formed by using the composition of the present invention. As described above, the film may be a film in which an organic EL material is contained as it is or a film containing a crosslink body of an organic EL material.

The constitution of the light emitting device of the present invention has, for example, electrodes consisting of an anode and a cathode and a film formed by using the composition of the present invention disposed between the electrodes.

[Layer Constitution]

The layer obtained by using the composition of the present invention is usually one or more selected from a light emitting layer, a hole transporting layer, a hole injection layer, an electron transporting layer and an electron injection layer, preferably a light emitting layer. These layers contain a light emitting material, a hole transporting material, a hole injection material, an electron transporting material and an electron injection material, respectively.

The light emitting device has a light emitting layer between an anode and a cathode. The light emitting device of the present invention preferably has at least one of a hole injection layer and a hole transporting layer between an anode and a light emitting layer from the standpoint of hole injectability and hole transportability, and preferably has at least one of an electron injection layer and an electron transporting layer between a cathode and a light emitting layer from the standpoint of electron injectability and electron transportability.

The material of a hole transporting layer, an electron transporting layer, a light emitting layer, a hole injection layer and an electron injection layer includes the above-described hole transporting materials, electron transporting materials, light emitting materials, hole injection materials and electron injection materials, respectively, in addition to the composition of the present invention.

When the material of a hole transporting layer, the material of an electron transporting layer and the material of a light emitting layer are soluble in a solvent which is used in forming a layer adjacent to the hole transporting layer, the electron transporting layer and the light emitting layer, respectively, in fabrication of a light emitting device, it is preferable that the materials have a crosslink group to avoid dissolution of the materials in the solvent. After forming the layers using the materials having a crosslink group, the layers can be substantially insolubilized in the solvent by crosslinking the crosslink group.

Methods of forming respective layers such as a light emitting layer, a hole transporting layer, an electron transporting layer, a hole injection layer, an electron injection layer and the like in the light emitting device of the present invention include, for example, a method of vacuum vapor deposition from a powder and a method of film formation from solution or melted state when a low molecular weight compound is used, and, for example, a method of film formation from solution or melted state when a polymer compound is used.

The order, number and thickness of layers to be laminated are regulated in consideration of light emission efficiency and luminance life.

[Substrate/Electrode]

The substrate in the light emitting device may advantageously be a substrate on which an electrode can be formed and which does not chemically change in forming an organic layer, and is a substrate made of a material such as, for example, glass, plastic, silicon and the like. In the case of an opaque substrate, it is preferable that an electrode most remote from the substrate is transparent or semi-transparent.

Then anode material includes, for example, electrically conductive metal oxides and semi-transparent metals, preferably, indium oxide, zinc oxide, tin oxide; electrically conductive compounds such as indium•tin•oxide (ITO), indium•zinc•oxide and the like; a composite of Ag, Pd and Cu (APC); NESA, gold, platinum, silver and copper.

The cathode material includes, for example, metals such as lithium, sodium, potassium, rubidium, cesium, beryllium, magnesium, calcium, strontium, barium, aluminum, zinc, indium and the like; alloys composed of two or more of them; alloys composed of at least one of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode each may take a laminated structure composed of two or more layers.

[Use]

For obtaining planar light emission using a light emitting device, a planar anode and a planar cathode may advantageously be disposed so as to overlap. For obtaining patterned light emission, a method of disposing a mask having a patterned window on the surface of a planar light emitting device, a method of forming a layer intending a no-emission portion extremely thick thereby attaining substantially no-emission, and a method of forming an anode or a cathode, or both electrodes, in the form of pattern, are listed. By forming a pattern by any of these methods and by disposing some electrodes so that independent ON/OFF is possible, a segment type display capable of displaying numerals, letters and the like is obtained. For obtaining a dot matrix display, it is advantageous that both an anode and a cathode are formed in the form of stripe and disposed so as to be orthogonalized. Partial color display and multi-color display become possible by a method of separately painting several kinds of polymer compounds of different emission colors and a method of using a color filter or a fluorescence conversion filter. A dot matrix display can be driven passively, or can be driven actively in combination with TFT and the like. These display devices can be used as a display of computers, television sets, mobile terminals and the like.

The planar light emitting device can be suitably used as a planar light source for backlight of liquid crystal displays or as a planar illumination light source. When a flexible substrate is used, it can be used also as a curved light source and a curved display.

EXAMPLES

The present invention will be illustrated further in detail by examples below, but the present invention is not limited to these examples.

In examples, the polystyrene-equivalent number-average molecular weight (Mn) and the polystyrene-equivalent weight-average molecular weight (Mw) of a polymer compound were determined by Size Exclusion Chromatography (SEC) (manufactured by Shimadzu Corporation, trade name: LC-10Avp). The measurement conditions of SEC are as described below.

[Measurement Condition]

A polymer compound to be measured was dissolved at a concentration of about 0.05 wt % in THF, and 10 µL of the solution was injected into SEC. THF was used as the mobile phase of SEC, and the solution was flowed at a flow rate of 2.0 mL/min. As the column, PLgel MIXED-B (manufactured by Polymer Laboratories Ltd.) was used. As the detector, an UV-VIS detector (manufactured by Shimadzu Corporation, trade name: SPD-10Avp) was used.

In the present examples, the shape of a film was measured using a noncontact three-dimensional surface shape measurement apparatus (manufactured by Zygo Corporation).

<Synthesis Example 1> Synthesis of Polymer Compound P1

[Chemical Formula 76]

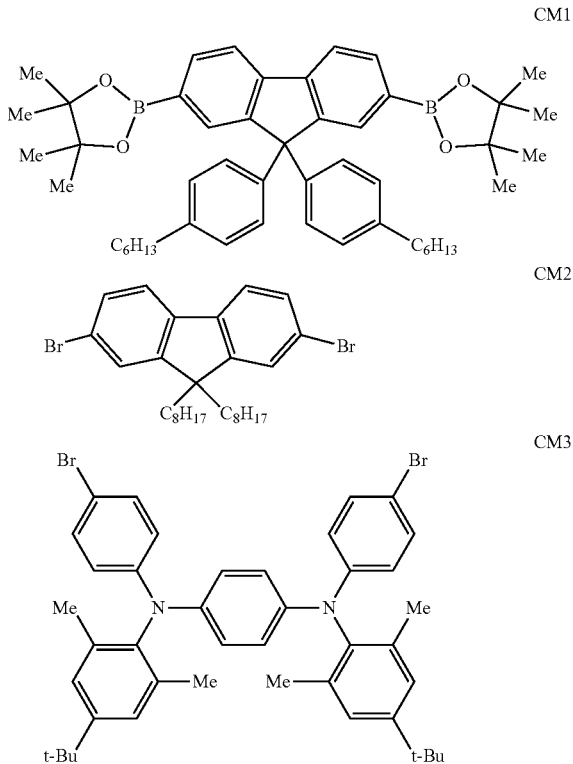

A monomer CM1 was synthesized according to a method described in International Publication WO2012/086671.

As a monomer CM2, a commercially available product was used.

A monomer CM3 was synthesized according to a method described in Japanese Patent Application National Publication No. 2004-143419.

An inert gas atmosphere was prepared in a reaction vessel, then, the monomer CM1 (13.4 g), the monomer CM2 (9.0 g), the monomer CM3 (1.3 g), tetraethylammonium hydroxide (43.0 g), palladium acetate (8 mg), tri(2-methoxyphenyl) phosphine (0.05 g) and toluene (200 mL) were added, and the mixture was heated to 90° C. and stirred at 90° C. for 8 hours. Thereafter, to this was added phenylboronic acid (0.22 g), and the mixture was stirred at 90° C. for 14 hours. The resultant reaction mixture was cooled down to room temperature, then, the aqueous layer was removed. Thereafter, to this was added a sodium diethyldithiocarbamate aqueous solution, and the mixture was stirred, then, the aqueous layer was removed. The resultant organic layer was washed with water and a 3 wt % acetic acid aqueous solution in this order. The resultant organic layer was dropped into methanol, to observe generation of a precipitate. The resultant precipitate was dissolved in toluene and purified by passing the solution through a silica gel column and an alumina column. The resultant toluene solution was dropped into methanol, to observe generation of a precipitate. The resultant precipitate was isolated by filtration and dried, to obtain 12.5 g of a polymer compound P1. The polymer compound P1 had a Mw of $3.1 \times 10^5$.

The polymer compound P1 is a copolymer constituted of a constitutional unit derived from the monomer CM1, a constitutional unit derived from the monomer CM2 and a constitutional unit derived from the monomer CM3 at a molar ratio of 50:45:5, according to the theoretical values calculated from the amounts of the charged raw materials.

<Example 1> Preparation of Composition 1

The polymer compound P1 (0.5 parts by weight), decylbenzene (manufactured by Tokyo Chemical Industry Co., Ltd.) (19.9 parts by weight), cyclohexylbenzene (manufactured by Tokyo Chemical Industry Co., Ltd.) (39.8 parts by weight) and 4-methylanisole (manufactured by Tokyo Chemical Industry Co., Ltd.) (39.8 parts by weight) were mixed. The resultant mixture was stirred, to prepare a composition 1 in which the polymer compound P1 was dissolved in a mixed solvent of decylbenzene, cyclohexylbenzene and 4-methylanisole.

<Example 2> Preparation of Composition 2

The polymer compound P1 (0.5 parts by weight), dodecylbenzene (manufactured by Tokyo Chemical Industry Co., Ltd.) (19.9 parts by weight), cyclohexylbenzene (manufactured by Tokyo Chemical Industry Co., Ltd.) (39.8 parts by weight) and 4-methylanisole (manufactured by Tokyo Chemical Industry Co., Ltd.) (39.8 parts by weight) were mixed. The resultant mixture was stirred, to prepare a composition 2 in which the polymer compound P1 was dissolved in a mixed solvent of dodecylbenzene, cyclohexylbenzene and 4-methylanisole.

<Comparative Example 1> Preparation of Composition C1

The polymer compound P1 (0.5 parts by weight), cyclohexylbenzene (manufactured by Tokyo Chemical Industry Co., Ltd.) (49.75 parts by weight) and 4-methylanisole (manufactured by Tokyo Chemical Industry Co., Ltd.) (49.75 parts by weight) were mixed. The resultant mixture was stirred, to prepare a composition C1 in which the polymer compound P1 was dissolved in a mixed solvent of cyclohexylbenzene and 4-methylanisole.

<Example D1> Fabrication and Evaluation of Film Shape Measurement Device D1

(Formation of Hole Injection Layer)

For formation of a hole injection layer, SHI2520-b10-IJ5 (manufactured by Nissan Chemical Industries, Ltd.) containing a hole injection material at a solid component concentration of 1.0 wt % was used. SHI2520-b10-IJ5 was introduced into an inkjet printing apparatus (manufactured by Litrex, 142P).

Next, SHI2520-b10-IJ5 was applied by an inkjet printing method on an ITO film (ITO film thickness: 45 nm) formed on a glass substrate and surrounded by a liquid repellent partition wall, and dried under reduced pressure environment (1 Pa), to form a film with a thickness of 35 nm. The resultant film was heated on a hot plate at 225° C. under an air atmosphere for 15 minutes, to form a hole injection layer.

(Formation of Hole Transporting Layer)

A hole transporting material 1 (polymer compound) was dissolved at a solid component concentration of 0.45 wt % in cyclohexylbenzene and 4-methylanisole (cyclohexylbenzene/4-methylanisole=79 wt %/21 wt %), to prepare a hole transporting material composition 1. The resultant hole transporting material composition 1 was introduced into an inkjet printing apparatus (manufactured by Litrex, 142P).

Next, the hole transporting material composition 1 was applied on the hole injection layer by an inkjet printing method, and dried under reduced pressure environment (1 Pa), to form a film with a thickness of 20 nm. The resultant film was heated on a hot plate at 195° C. under a nitrogen gas atmosphere for 60 minutes, to form a hole transporting layer.

(Formation of Light Emitting Layer)

A green light emitting material 1 (containing an iridium complex and a polymer host) was dissolved at a solid component concentration of 1.8 wt % indecylbenzene, cyclohexylbenzene and 4-methylanisole (decylbenzene/cyclohexylbenzene/4-methylanisole=18.3 wt %/40.2 wt %/41.5 wt %), to prepare a green light emitting material composition 1. The resultant green light emitting material composition 1 was introduced into an inkjet printing apparatus (manufactured by Litrex, 120L).

Next, the green light emitting material composition 1 was applied on the hole transporting layer by an inkjet printing method, and dried under reduced pressure environment (1 Pa), to form a film with a thickness of 80 nm. The resultant film was heated on a hot plate at 145° C. under a nitrogen gas atmosphere for 10 minutes, to form a light emitting layer.

(Formation of Cathode)

A cathode was formed by placing the glass substrate carrying the light emitting layer formed thereon in a vapor deposition machine, reducing the pressure in the vapor deposition machine down to $1.0 \times 10^{-4}$ Pa or lower, then, vapor-depositing aluminum with a thickness of about 30 nm on the light emitting layer, to fabricate a film shape measurement device D1.

(Measurement of Shape of Film)

The shape of a film of the film shape measurement device D1 was measured. The measurement results are shown in FIG. 1. An area having a thickness of +5 nm with respect to the thinnest thickness in a pixel area surrounded by a liquid repellent partition wall was evaluated, to find a proportion of 22% in the pixel area surrounded by a liquid repellent partition wall.

<Comparative Example CD1> Fabrication and Evaluation of Film Shape Measurement Device CD1

(Formation of Hole Injection Layer and Hole Transporting Layer)

A hole injection layer and a hole transporting layer were formed, in the same manner as in Example D1.

(Formation of Light Emitting Layer)

A green light emitting material 1 (containing an iridium complex and a polymer host) was dissolved at a solid component concentration of 1.8 wt % in cyclohexylbenzene and 4-methylanisole (cyclohexylbenzene/4-methylanisole=79 wt %/21 wt %), to prepare a green light emitting material composition C1. The resultant green light emitting material composition C1 was introduced into an inkjet printing apparatus (manufactured by Litrex, 142P).

Next, the green light emitting material composition C1 was applied on the hole transporting layer by an inkjet printing method, and dried under reduced pressure environment (1 Pa), to form a film with a thickness of 80 nm. The resultant film was heated on a hot plate at 145° C. under a nitrogen gas atmosphere for 10 minutes, to form a light emitting layer.

(Formation of Cathode)

A cathode was formed in the same manner as in Example D1, to fabricate a film shape measurement device CD1.

(Measurement of Shape of Film)

The shape of a film of the film shape measurement device CD1 was measured. The measurement results are shown in FIG. 1. An area having a thickness of +5 nm with respect to the thinnest thickness in a pixel area surrounded by a liquid repellent partition wall was evaluated, to find a proportion of 16% in the pixel area surrounded by a liquid repellent partition wall.

<Example D2> Fabrication and Evaluation of Film Shape Measurement Device D2

(Formation of Hole Injection Layer and Hole Transporting Layer)

A hole injection layer and a hole transporting layer were formed, in the same manner as in Example D1.

(Formation of Light Emitting Layer)

A blue light emitting material 2 (polymer compound) was dissolved at a solid component concentration of 0.8 wt % in decylbenzene, cyclohexylbenzene and 4-methylanisole (decylbenzene/cyclohexylbenzene/4-methylanisole=18.3 wt %/40.2 wt %/41.5 wt %), to prepare a blue light emitting material composition 2. The resultant blue light emitting material composition 2 was introduced into an inkjet printing apparatus (manufactured by Litrex, 120L).

Next, the blue light emitting material composition 2 was applied on the hole transporting layer by an inkjet printing method, and dried under reduced pressure environment (1 Pa), to form a film with a thickness of 65 nm. The resultant film was heated on a hot plate at 145° C. under a nitrogen gas atmosphere for 10 minutes, to form a light emitting layer.

(Formation of Cathode)

A cathode was formed in the same manner as in Example D1, to fabricate a film shape measurement device D2.

(Measurement of Shape of Film)

The shape of a film of the film shape measurement device D2 was measured. The measurement results are shown in FIG. 2. An area having a thickness of +5 nm with respect to the thinnest thickness in a pixel area surrounded by a liquid repellent partition wall was evaluated, to find a proportion of 45% in the pixel area surrounded by a liquid repellent partition wall.

<Comparative Example CD2> Fabrication and Evaluation of Film Shape Measurement Device CD2

(Formation of Hole Injection Layer and Hole Transporting Layer)

A hole injection layer and a hole transporting layer were formed, in the same manner as in Example D1.

(Formation of Light Emitting Layer)

A blue light emitting material 2 (polymer compound) was dissolved at a solid component concentration of 0.8 wt % in cyclohexylbenzene and 4-methylanisole (cyclohexylbenzene/4-methylanisole=79 wt %/21 wt %), to prepare a blue light emitting material composition C2. The resultant blue light emitting material composition C2 was introduced into an inkjet printing apparatus (manufactured by Litrex, 142P).

Next, the blue light emitting material composition C2 was applied on the hole transporting layer by an inkjet printing method, and dried under reduced pressure environment (1 Pa), to form a film with a thickness of 65 nm. The resultant film was heated on a hot plate at 145° C. under a nitrogen gas atmosphere for 10 minutes, to form a light emitting layer.

(Formation of Cathode)

A cathode was formed in the same manner as in Example D1, to fabricate a film shape measurement device CD2.

(Measurement of Shape of Film)

The shape of a film of the film shape measurement device CD2 was measured. The measurement results are shown in FIG. 2. An area having a thickness of +5 nm with respect to the thinnest thickness in a pixel area surrounded by a liquid repellent partition wall was evaluated, to find a proportion of 30% in the pixel area surrounded by a liquid repellent partition wall.

INDUSTRIAL APPLICABILITY

The present invention can provide a composition containing an organic EL material and a solvent which, when used in a discharge type application method, is useful for production of a film excellent in flatness. According to the present invention, a light emitting device having a film formed by using the composition can be provided.

The invention claimed is:

1. A composition comprising
   an organic EL material, wherein the organic EL material contains an iridium complex and a host material,
   a solvent (A) represented by the formula (1),
   an aromatic hydrocarbon solvent (B), wherein the aromatic hydrocarbon solvent (B) is a benzene derivative having a total number of carbon atoms of 7 to 15 and substituted with an alkyl group or a cycloalkyl group, and
   an aromatic ether solvent (C) wherein the aromatic ether solvent (C) is at least one selected from the group consisting of: alkylaryl ethers having a total number of carbon atoms of 7 to 15 and in which the aryl portion is optionally substituted with an alkyl group; and diaryl ethers having a total number of carbon atoms of 12 to 15 and optionally substituted with an alkyl group:

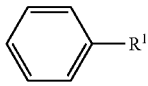
(1)

wherein $R^1$ represents an alkyl group having a number of carbon atoms of 10 to 12; and wherein the content of the solvent (A): wtA (by weight), the content of the aromatic hydrocarbon solvent (B): wtB (by weight) and the content of the aromatic ether solvent (C): wtC (by weight) satisfy the formula (1-1):

$$0.05 \leq wtA/(wtA+wtB+wtC) \leq 0.50 \quad (1\text{-}1).$$

2. The composition according to claim 1, wherein $R^1$ is an alkyl group having a number of carbon atoms of 10.

3. The composition according to claim 1, wherein aromatic hydrocarbon solvent (B) is pentylbenzene, hexylbenzene, heptylbenzene, octylbenzene, nonylbenzene, cyclohexylbenzene or tetralin.

4. The composition according to claim 1, wherein the aromatic ether solvent (C) is methylanisole, dimethylanisole, ethylanisole, butyl phenyl ether, butylanisole, pentylanisole, hexylanisole, heptylanisole, octylanisole or phenoxytoluene.

5. The composition according to claim 1, wherein the host material is a polymer compound containing at least one constitutional unit selected from the group consisting of a constitutional unit represented by the formula (X) and a constitutional unit represented by the formula (Y):

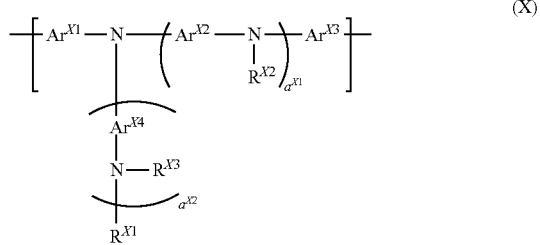
(X)

wherein
- $a^{X1}$ and $a^{X2}$ each independently represent an integer of 0 or more;
- $Ar^{X1}$ and $Ar^{X3}$ each independently represent an arylene group or a divalent heterocyclic group, and the forgoing groups optionally have a substituent;
- $Ar^{X2}$ and $Ar^{X4}$ each independently represent an arylene group, a divalent heterocyclic group or a divalent group in which at least one arylene group and at least one divalent heterocyclic group are bonded directly, and the forgoing groups optionally have a substituent, when a plurality of $Ar^{X2}$ and $Ar^{X4}$ are present, they may be the same or different at each occurrence;
- $R^{X1}$, $R^{X2}$ and $R^{X3}$ each independently represent a hydrogen atom, an alkyl group, a cycloalkyl group, an aryl group or a monovalent heterocyclic group, and the forgoing groups optionally have a substituent, when a plurality of R and $R^{X3}$ are present, they may be the same or different at each occurrence; and $$-\!\!\!+\!\!Ar^{Y1}\!\!+\!\!- \quad (Y)$$

wherein $Ar^{Y1}$ represents an arylene group, a divalent heterocyclic group or a divalent group in which at least one arylene group and at least one divalent heterocyclic group are bonded directly, and the forgoing groups optionally have a substituent.

6. The composition according to claim 1, wherein the iridium complex is an iridium complex represented by the formula (Ir-1), an iridium complex represented by the formula (Ir-2), an iridium complex represented by the formula (Ir-3), an iridium complex represented by the formula (Ir-4) or an iridium complex represented by the formula (Ir-5):

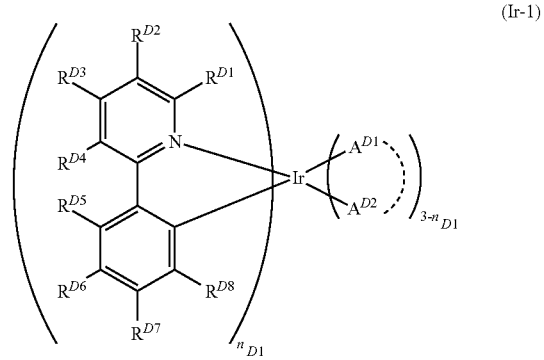
(Ir-1)

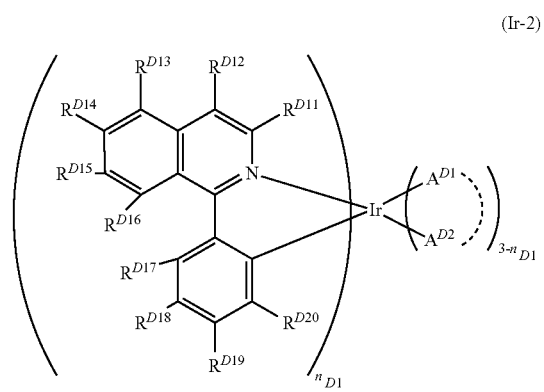
(Ir-2)

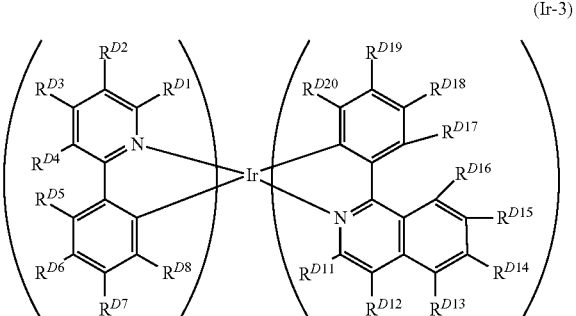
(Ir-3)

-continued

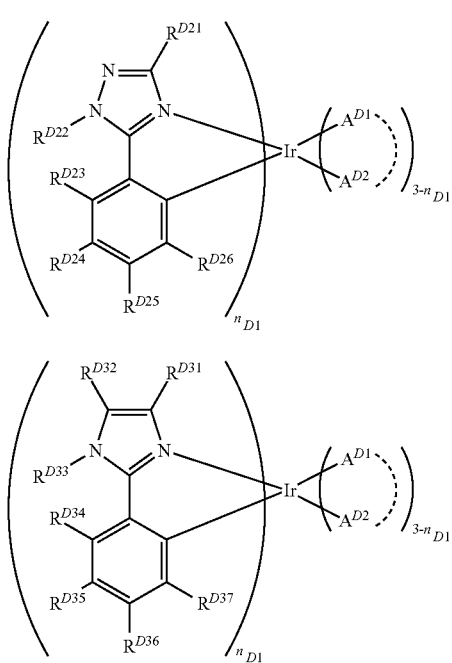

(Ir-4)

(Ir-5)

wherein $n_{D1}$ represents 1, 2 or 3, $n_{D2}$ represents 1 or 2, $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$ and $R^{D37}$, each independently represent a hydrogen atom, an alkyl group, a cycloalkyl group, an alkoxy group, a cycloalkoxy group, an aryl group, an aryloxy group, a monovalent heterocyclic group or a halogen atom, and the forgoing groups optionally have a substituent, when a plurality of $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$ and $R^{D37}$ are present, they may be the same or different at each occurrence; and -$A^{D1}$-$A^{D2}$- represents an anionic bidentate ligand, $A^{D1}$ and $A^{D2}$ each independently represent a carbon atom, an oxygen atom or a nitrogen atom bonding to an iridium atom, and these atoms may be ring constituent atoms, when a plurality of -$A^{D1}$-$A^{D2}$- are present, they may be the same or different.

7. A light emitting device comprising a film formed by using the composition according to claim 1.

8. A film formed surrounded by a liquid repellent partition wall by using the composition according to claim 1.

\* \* \* \* \*